US012036092B2

(12) United States Patent
Raby et al.

(10) Patent No.: US 12,036,092 B2
(45) Date of Patent: Jul. 16, 2024

(54) COMBINING DATA FROM MULTIPLE DENTAL ANATOMY SCANS

(71) Applicant: Solventum Intellectual Properties Company, Maplewood, MN (US)

(72) Inventors: Richard E. Raby, Lino Lakes, MN (US); Eric S. Hansen, Apex, NC (US); Joseph R. Dufour, Cottage Grove, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 358 days.

(21) Appl. No.: 17/417,508

(22) PCT Filed: Nov. 6, 2019

(86) PCT No.: PCT/IB2019/059553
§ 371 (c)(1),
(2) Date: Jun. 23, 2021

(87) PCT Pub. No.: WO2020/141366
PCT Pub. Date: Jul. 9, 2020

(65) Prior Publication Data
US 2022/0110723 A1 Apr. 14, 2022

Related U.S. Application Data

(60) Provisional application No. 62/787,025, filed on Dec. 31, 2018.

(51) Int. Cl.
*A61C 9/00* (2006.01)
*G06T 7/00* (2017.01)
(Continued)

(52) U.S. Cl.
CPC .......... *A61C 9/0053* (2013.01); *G06T 7/0012* (2013.01); *G06T 7/11* (2017.01);
(Continued)

(58) Field of Classification Search
CPC . B60K 6/40; B60K 6/38; B60K 6/387; B60K 6/405; B60K 6/48; B60K 6/547;
(Continued)

(56) References Cited

U.S. PATENT DOCUMENTS

2008/0020350 A1 1/2008 Matov et al.
2009/0316966 A1 12/2009 Marshall et al.
(Continued)

FOREIGN PATENT DOCUMENTS

CN 108765474 11/2018
JP 2008/513094 5/2008
(Continued)

OTHER PUBLICATIONS

Machine translation for KR 2015-0016194 (Year: 2015).*
(Continued)

*Primary Examiner* — Qian Yang

(57) ABSTRACT

A method to combine dental anatomy data includes, by the use of a computing device: receiving volumetric dental data and superficial dental data; segmenting the crowns of the volumetric dental data from the roots of the volumetric dental data; segmenting the crowns of the superficial dental data from the gingiva of the superficial dental data; transforming superficial dental data of the crowns to substantially align with volumetric dental data of the crowns; stitching the transformed superficial dental data of the crowns to volumetric dental data of the crowns; and outputting for display an image data based on the combined dental data.

20 Claims, 21 Drawing Sheets

(51) Int. Cl.
*G06T 7/11* (2017.01)
*G06T 7/33* (2017.01)
*G06T 7/37* (2017.01)
*G06T 17/20* (2006.01)
*G16H 30/40* (2018.01)

(52) U.S. Cl.
CPC ............... *G06T 7/33* (2017.01); *G06T 7/37* (2017.01); *G06T 17/20* (2013.01); *G16H 30/40* (2018.01); *G06T 2207/10028* (2013.01); *G06T 2207/10081* (2013.01); *G06T 2207/10088* (2013.01); *G06T 2207/30036* (2013.01); *G06T 2210/41* (2013.01)

(58) Field of Classification Search
CPC .. F16D 13/683; F16D 25/0638; F16H 57/021; F16H 57/0424; F16H 57/043; F16H 57/0471; F16H 57/0472; F16H 2057/02034; F16H 2057/02043; Y02T 10/62; Y02T 10/64; Y02T 10/7072; Y02T 10/72; H02K 7/003; H02K 7/083; H02K 7/006; H02K 7/108; H02K 9/19; B60L 50/16
See application file for complete search history.

(56) References Cited

U.S. PATENT DOCUMENTS

| | | | |
|---|---|---|---|
| 2011/0268327 A1 | 11/2011 | Getto et al. | |
| 2014/0169648 A1 | 6/2014 | Andreiko | |
| 2014/0227655 A1 | 8/2014 | Andreiko et al. | |
| 2014/0272772 A1 | 9/2014 | Andreiko et al. | |
| 2016/0220200 A1 | 8/2016 | Sandholm et al. | |
| 2016/0374784 A1 | 12/2016 | Joshi et al. | |
| 2017/0105817 A1* | 4/2017 | Chun | A61C 7/12 |

FOREIGN PATENT DOCUMENTS

| | | | |
|---|---|---|---|
| JP | 2014/117611 | | 2/2018 |
| JP | 2018/520804 | | 12/2020 |
| KR | 20120081578 | | 7/2012 |
| KR | 2015-0016194 | * | 2/2015 |
| WO | WO 2004/098379 | * | 11/2004 |
| WO | 2008128700 | | 10/2008 |
| WO | WO 2011-133662 | | 10/2011 |
| WO | WO 2018-111491 | | 6/2018 |

OTHER PUBLICATIONS

Extended European Search Report, EP19907425.3, Aug. 5, 2022, 3 Pages.
Hong-Tzong Yau et al., "Tooth model reconstruction based upon data fusion for orthodontic treatment simulation", Computers in Biology and Medicine, New York, vol. 48, Feb. 18, 2014, pp. 8-16.
Jung, "Combining volumetric dental CT and optical scan data for 1-20 teeth modelling", CAD Computer Aided Design, May 7, 2015, vol. 67-68, pp. 24-37.
International Search Report for PCT International Application No. PCT/IB2019/059553, mailed on Dec. 10, 2019, 4 pages.

* cited by examiner

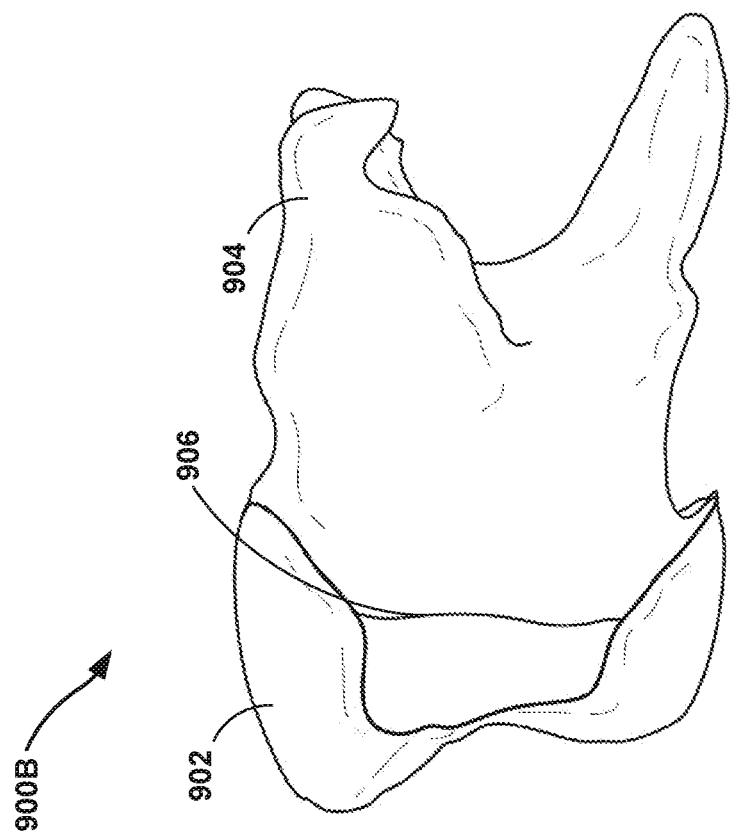
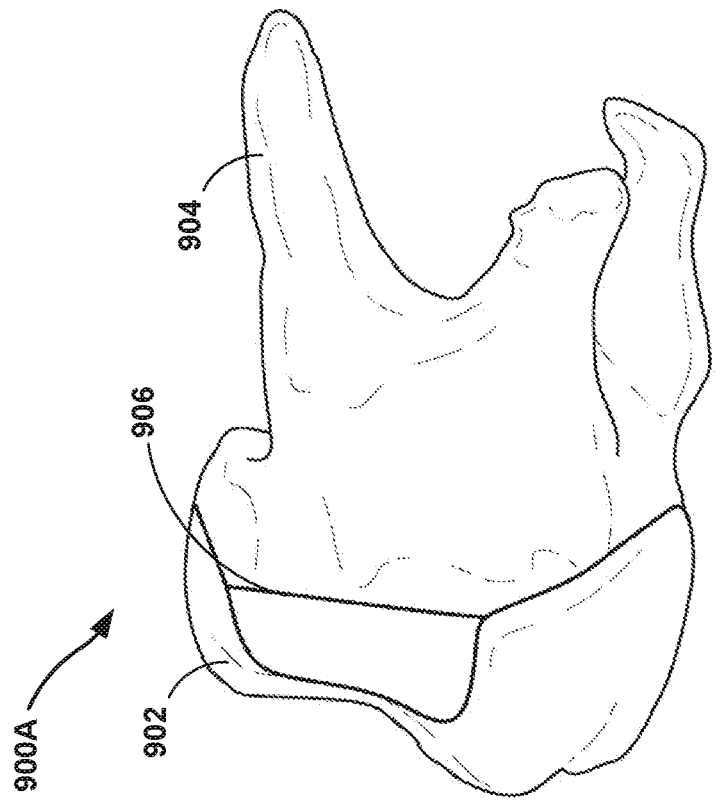

COMBINING DATA FROM MULTIPLE DENTAL ANATOMY SCANS

CROSS REFERENCE TO RELATED APPLICATIONS

This application is a national stage filing under 35 U.S.C. 371 of PCT/IB2019/059553, filed Nov. 6, 2019, which claims the benefit of U.S. Provisional Application No. 62/787,025, filed Dec. 31, 2018, the disclosures of which are incorporated by reference in their entireties herein.

TECHNICAL FIELD

This disclosure relates to dental imaging, specifically systems and techniques used to manipulate data obtained from dental imaging processes.

BACKGROUND

The field of orthodontics relates to repositioning a patient's teeth for improved function and aesthetic appearance. Orthodontic treatments using braces or alignment trays benefit from imaging of the dental anatomy of the patient, such as the teeth, tooth roots, or other portions of the dental anatomy. Imaging of the dental anatomy of the patient may be performed using various imaging systems and techniques. Data obtained from two or more different imaging devices may be combined to provide a more comprehensive image of the dental anatomy of the patient.

SUMMARY

Combining dental anatomy data from two or more different imaging devices, such as combining superficial dental anatomies with sub-gingival dental anatomies originating from difference scan sources, may include transforming portions of a first data set to align with corresponding portions of a second data set to reduce distortion of features of the dental anatomy. For example, a computing device for combining dental anatomy data may be configured to receive first dental data indicative of a three-dimensional dental anatomy of a patient and second dental data indicative of the three-dimensional dental anatomy of the patient. The computing device may be configured to segment a first subset of the first dental data from a second subset of the first dental data. At least a portion of the second dental data may correspond to the first subset of the first dental data. For example, the second dental data and the first subset of the first dental data may be indicative of the same portions of the dental anatomy of the patient. The computing device may be configured to transform the corresponding portion of the second dental data to substantially align with the first dental data. The computing device may be configured to generate combined dental data by replacing the first subset of the first dental data with the transformed second dental data to stitch the transformed second dental data to the second subset of the second dental data. The computing device may be configured to output for display image data based on the combined dental data.

In some examples, a method may include receiving, by a computing device, volumetric dental data indicative of a three-dimensional sub-gingival dental anatomy of a patient; receiving, by the computing device, superficial dental data indicative of a three-dimensional superficial dental anatomy of the patient; segmenting, by the computing device, a first subset of the volumetric dental data representative of crowns of teeth of the patient from a second subset of the volumetric dental data representative of roots of the teeth, where the first subset of the volumetric dental data is indicative of a first spatial orientation of the crowns, and where the second subset of the volumetric dental data is indicative of a spatial orientation of the roots; segmenting, by the computing device, a first subset of the superficial dental data representative of the crowns from a second subset of the superficial dental data representative of the gingiva of the patient, where the first subset of the superficial dental data is indicative of a second spatial orientation of the crowns, and where the second subset of the superficial dental data is indicative of a spatial orientation of the gingiva; transforming, by the computing device, the first subset of the superficial dental data indicative of the second spatial orientation of the crowns such that the second spatial orientation of the crowns substantially aligns with the first spatial orientation of the crowns; generating, by the computing device, combined dental data by replacing the first subset of the subgingival data indicative of the first spatial orientation of the crowns with the transformed first subset of the superficial dental data indicative of the second spatial orientation of the crowns to stitch the transformed first subset of the superficial dental data indicative of the second spatial orientation of the crowns to the second subset of the volumetric dental data representative of the roots; and outputting, by the computing device and for display, image data based on the combined dental data.

In some examples, a method may include receiving, by a computing device, first dental data indicative of a first three-dimensional dental anatomy of a patient; receiving, by the computing device, second dental data indicative of a second three-dimensional dental anatomy of the patient; segmenting, by the computing device, a first subset of the first dental data from a second subset of the first dental data, where at least a portion of the second dental data corresponds to the first subset of the first dental data; transforming, by the computing device, the corresponding portion of the second dental data to substantially align with the first dental data; generating, by the computing device, combined dental data by replacing the first subset of the first dental data with the transformed corresponding portion of the second dental data to stitch the transformed second dental data to the second subset of the second dental data; and outputting, by the computing device and for display, image data based on the combined dental data.

In some examples, a non-transitory computer-readable storage medium that stores computer system-executable instructions that, when executed, configure a processor to: receive volumetric dental data indicative of a three-dimensional sub-gingival dental anatomy of a patient; receive superficial dental data indicative of a three-dimensional superficial dental anatomy of the patient; segment a first subset of the volumetric dental data representative of crowns of teeth of the patient from a second subset of the volumetric dental data representative of roots of the teeth, where the first subset of the volumetric dental data is indicative of a first spatial orientation of the crowns, and where the second subset of the volumetric dental data is indicative of a spatial orientation of the roots; segment a first subset of the superficial dental data representative of the crowns from a second subset of the superficial dental data representative of the gingiva of the patient, where the first subset of the superficial dental data is indicative of a second spatial orientation of the crowns, and where the second subset of the superficial dental data is indicative of a spatial orientation of the gingiva; transform the first subset of the superficial dental data indicative of the second spatial orientation of the crowns such that the second spatial orientation of the crowns substantially aligns with the first spatial orientation of the crowns; generate combined dental data by replacing the first subset of the sub-gingival data indicative of the first spatial orientation of the crowns with the transformed first subset of the superficial dental data indicative of the second spatial orientation of the crowns to stitch the transformed first subset of the superficial dental data indicative of the second spatial orientation of the crowns to the second subset of the volumetric dental data representative of the roots; and output, for display, image data based on the combined dental data.

The details of one or more examples of this disclosure are set forth in the accompanying drawings and the description below. Other features, objects, and advantages of this disclosure will be apparent from the description and drawings, and from the claims.

BRIEF DESCRIPTION OF THE DRAWINGS

FIGS. 10A and 10B are example images representing a best-fit registration of a crown (e.g., of superficial dental data) to a tooth root (e.g., a root of volumetric dental data).

DETAILED DESCRIPTION

Figure 1:
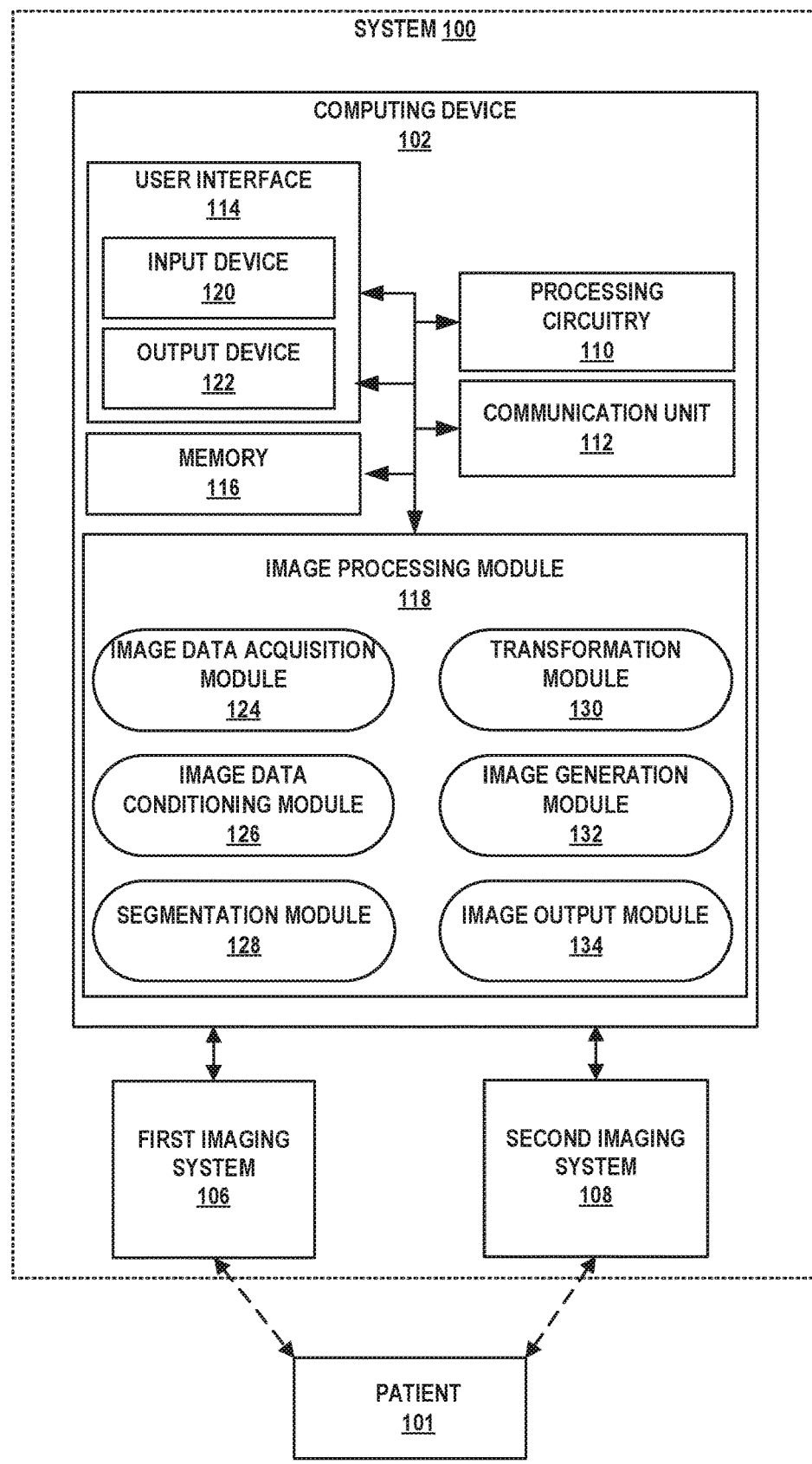
FIG. 1 is a conceptual diagram illustrating an example system configured to combine data of a dental anatomy of a patient.

The systems and techniques described herein may be used to combine dental anatomy data from different types of scans with improved global accuracy (in terms of tooth position and orientation) and the alignment at the joint of the images. Combining dental anatomy data from two or more different imaging devices, such as combining first data set including sub-gingival dental anatomies with second data set including superficial dental anatomies originating from difference scan sources, may include transforming portions of the first data set to align with corresponding portions of the second data set to reduce distortion of features of the dental anatomy.

Dental imaging systems may capture superficial dental anatomies, sub-gingival dental anatomies, or both. Superficial dental anatomies include an anatomy of teeth of a patient above the gingiva, such as surface contours and spacing of the teeth. Sub-gingival dental anatomies include an anatomy of the teeth of the patient below the gingiva, such as tooth roots, alveolar bone, and cortical bone. Some dental imaging systems may capture more accurate images of superficial dental anatomies or sub-gingival dental anatomies. For example, an intra-oral scanner, such as the 3M True Definition Scanner, may produce higher resolution images of superficial dental anatomies compared to other dental imaging systems. In contrast, a Cone Beam Computed Tomography (CBCT, 3D X-ray) scanner or Magnetic Resonance Imaging (MRI) scanner may produce higher resolution images of sub-gingival dental anatomies compared to other dental imaging systems. In some examples, CBCT, 3D X-ray, or MRI may produce images having a greater global accuracy across the scan volume due to rigid fixturing of components within the scanner, e.g., a patient may be held in fixed relation to the scanner during scanning, which also improves global accuracy. Additionally, or alternatively, some dental imaging systems may be capable of capturing both superficial dental anatomies and sub-gingival dental anatomies but may produce higher resolution images of either superficial dental anatomies or sub-gingival dental anatomies. Additionally, or alternatively, some dental imaging systems may more accurately represent a position of the teeth in three-dimensional space (e.g., global accuracy), but with relatively less resolution compared to other dental imaging systems. For example, CBCT and MRI scanners may have higher global accuracy, but poorer resolution of surface detail compared to intra-oral scanners. In contrast, intra-oral scanners may have higher resolution of surface detail, but poorer global accuracy compared to CBCT and MRI scanners due to accumulated errors as numerous patches of scan data are stitched together into a dental arch.

Combining data associated with crowns from an intra-oral scan with data associated with roots from a CBCT scan may provide higher resolution imagery of both portions of the teeth. However, combining data associated with crowns from an intra-oral scan with data associated with roots from a CBCT scan may result in incorrect registration and/or misalignment between the roots and crowns for given teeth in the resulting combined image. This incorrect registration and/or misalignment may be due to distortion in the intra-oral scan and error in local registration of features between scan types due to a lack of detail in the CBCT scan. The incorrect registration and/or misalignment may result in a visible discontinuity in the resulting image, e.g., steps, between crowns and roots where the data sets are combined, e.g., "stitched" together.

In some examples, the systems and techniques described herein enable improved integration between the different data sets by unwarping the intra-oral scan and aligning it to the CBCT (or MRI) scan. Additionally, or alternatively, the systems and techniques describe herein may improve the utility of CBCT scans in orthodontic treatment planning by more accurately depicting the global positions of the crowns in the mouth; allowing clinicians to plan setups and tooth movements with greater confidence that roots are not interfering with one another, and/or with one or more of implants, mini-screws, or cortical bone.

FIG. 1 is a conceptual diagram illustrating an example system 100 configured to combine data of a dental anatomy of patient 101. System 100 includes a computing device 102 configured to receive, from a first imaging device 106, first dental data indicative of a three-dimensional dental anatomy of patient 101 and receive, from a second imaging device 108, second dental data indicative of the three-dimensional dental anatomy of patient 101. System 100 may include additional components that, for clarity, are not shown in FIG. 1. For example, system 100 may include a power supply to provide power to the components of system 100. Similarly, the components of system 100 shown in FIG. 1 may not be necessary in every example of system 100.

Computing device 102 may include, for example, a desktop computer, a laptop computer, a tablet computer, a workstation, a server, a mainframe, a cloud computing system, or the like. Computing device 102 is configured to receive from first imaging device 106 volumetric dental data and receive from second imaging device 108 superficial dental data. In some examples, computing device 102 may be configured to control first imaging device 106 and second imaging device 108. For example, computing device 102 may be configured to cause first imaging device 106 and/or second imaging device 108 to acquire respective volumetric dental data and/or superficial dental data. In the example of FIG. 1, computing device 102 includes processing circuitry 110, communications unit 112, user interface 114, memory 116, and image processing modules 118. In some examples, computing device 102 may include additional components or fewer components than those illustrated in FIG. 1.

Processing circuitry 110 is configured to implement functionality and/or process instructions for execution within computing device 102. Processing circuitry 110, as well as other processors, controllers, control circuitry, and the like, described herein, may include one or more processors. Processing circuitry 110 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Communication units 112 may be configured to communicate with external devices (e.g., first imaging device 106, second imaging device 108, or a server) via one or more networks, such as one or more wired or wireless networks. Communication unit 112 may be a network interface card, such as an Ethernet card, an optical transceiver, a radio frequency transceiver, or any other type of device that can send and receive information. Other examples of such network interfaces may include Wi-Fi radios or USB. In some examples, computing device 102 utilizes communication units 112 to wirelessly communicate with an external device.

User interface 114 includes input devices 120 and output devices 122. Input device 120 may include one or more input devices configured to receive input from a user through tactile, audio, or video sources. Examples of input device 120 include, but are not limited to, a mouse, a keyboard, a voice responsive system, video camera, microphone, touchscreen, or a device for detecting a command from a user. Output device 122 may include one or more output devices configured to provide output to a user using audio or video media. Examples of output device 122 may include, but are not limited to, a display, a sound card, a video graphics adapter card, or a device for converting a signal into an appropriate form understandable to humans or machines.

Memory 116 may be configured to store information within computing device 102 during operation. Memory 116 may include a computer-readable storage medium or computer-readable storage device. In some examples, memory 116 may store program instructions. The program instructions may include one or more program modules that are executable by processing circuitry 110. When executed by processing circuitry 110, such program instructions may cause processing circuitry 110 to provide the functionality ascribed to it herein. The program instructions may be embodied in software, firmware, and/or RAMware. Memory 120 may include any one or more of volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Computing device 102 may be communicatively coupled to first imaging device 106 and second imaging device 108 using respective communication connections. In some examples, the communication connection may include a network link, such as Ethernet or other network connections. Such connection may be wireless connection, a wired connection, or a combination of both. In some examples, the communications connections may include other types of device connections, such as, USB, IEEE 1394, or the like. For example, computing device 102 may be communicatively coupled to first imaging device 106 and second imaging device 108 via wired or wireless.

First imaging device 106 may be configured to acquire digital image data including volumetric dental data indicative of a three-dimensional sub-gingival dental anatomy of patient 101. First imaging device 106 may include a cone beam computed tomography (CBCT) scanner, a magnetic resonance image (MRI) scanner, or an imaging device configured to produce digital image data that may penetrate and distinguish between different types of dental anatomy tissues. Sub-gingival dental anatomies include an anatomy of the teeth of patient 101 above and below the gingiva. For example, the sub-gingival dental anatomy may include teeth, tooth roots, alveolar bone, and cortical bone. In some examples, the sub-gingival dental anatomy may include at least one of a maxilla, a mandible, or a portion of a skull of patient 101.

Figure 2:
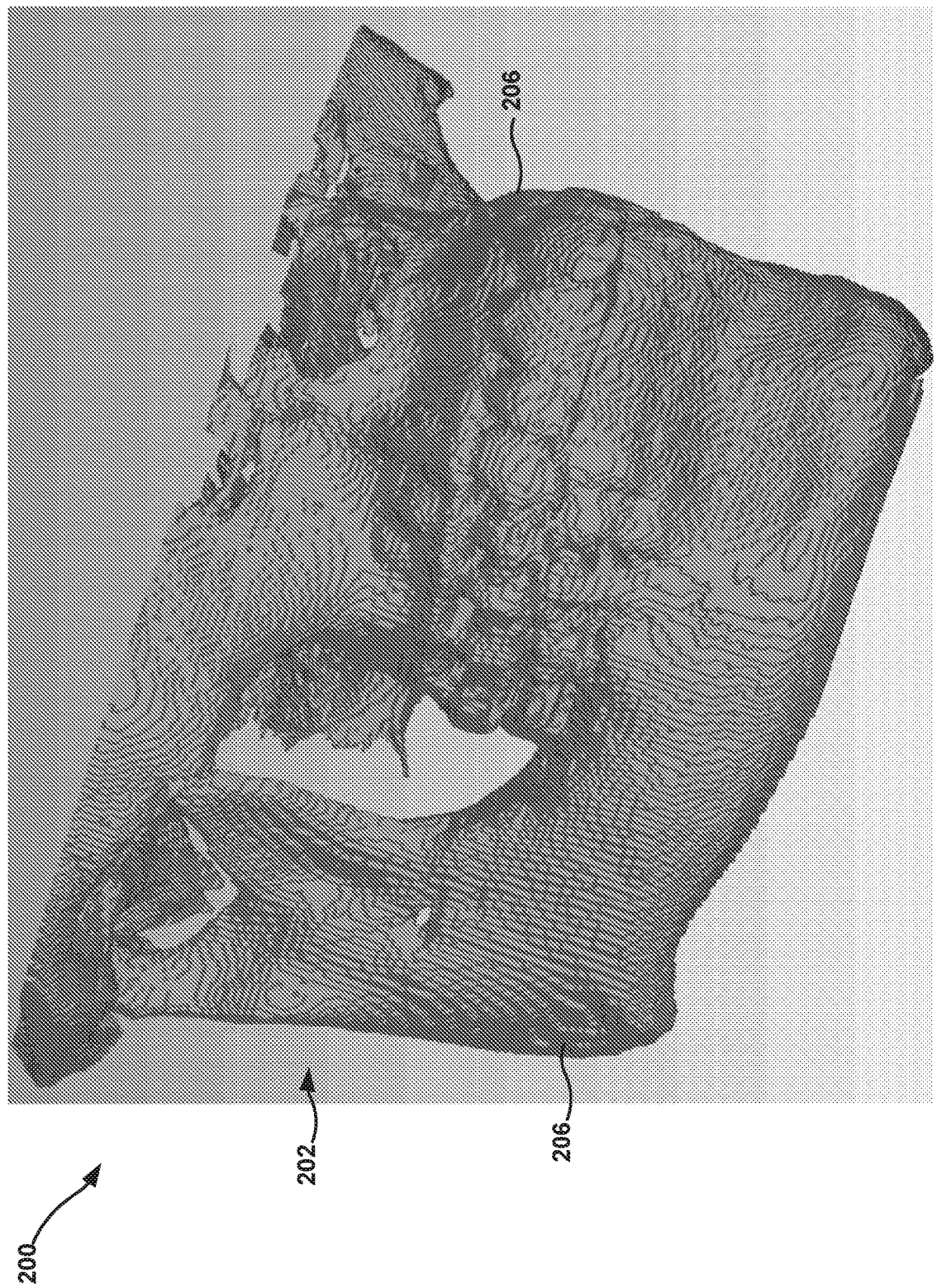
FIG. 2 illustrates an example digital image generated using volumetric dental data indicative of a three-dimensional sub-gingival dental anatomy of a patient.

FIG. 2 illustrates an example digital image 200 generated using volumetric dental data indicative of a three-dimensional sub-gingival dental anatomy of patient 101. Digital image 200 representative of volumetric dental data acquired from a CBCT scan of an inferior portion of a skull 202 of patient 101, including maxilla 204 and mandible 206, represented in DICOM image file format. In some examples, first imaging device 106 may be configured to generate volumetric dental data that includes a density-weighted point cloud. The density-weight point cloud may be used to resolve hard tissues of the sub-gingival dental anatomy and soft tissues of the sub-gingival dental anatomy. For example, the hard tissues may include at least one of enamel, dentin, cementum, alveolar bone, or cortical bone. The soft tissues may include at least one of hard palate, gingiva, tongue, oral mucosa, periodontal ligaments, cartilage, muscle, or skin. In this way, first imaging device 106 may generate volumetric dental data that includes a first subset representative of a first tissue and a second subset representative of a second tissue.

In some examples, computing device 102, e.g., processing circuitry 110, may be configured to filter the volumetric dental data using at least one density threshold based on at least one density of at least one of the hard tissues or the soft tissues. In some examples, first imaging device 106 may include pre-processing circuitry configured to filter the sub-gingival data. The at least one density threshold may include an upper density limit and a lower density limit of at least one tissue of the dental anatomy. For example, the at least one density threshold may include an upper density limit and a lower density limit of at least one of enamel, dentin, cementum, alveolar bone, cortical bone, hard palate, gingiva, tongue, oral mucosa, periodontal ligaments, cartilage, muscle, or skin. In the example of digital image 200, soft tissues have been filtered out, so only hard tissues, such as enamel and cortical bone, are illustrated. Other hard tissues, such as alveolar bone, dentin, and enamel, may be present but not visible due to obstruction by the superior dental structures.

Figure 3:
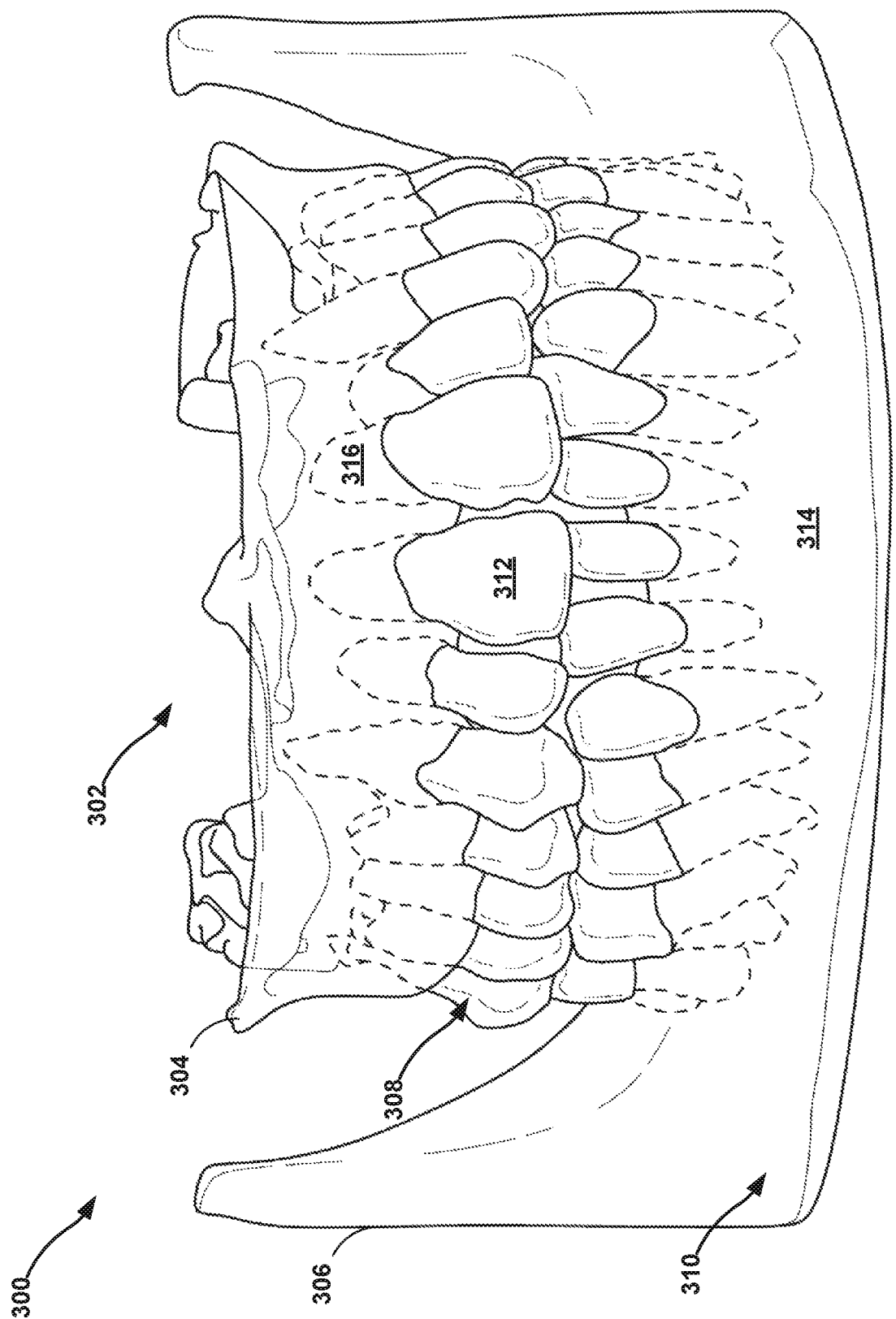
FIG. 3 illustrates an example digital image generated using volumetric dental data indicative of a three-dimensional sub-gingival dental anatomy of a patient.

In some examples, more than one hard tissue represented by the density-weighted point cloud may be resolved on a single digital image. For example, FIG. 3 illustrates an example digital image 300 generated using volumetric dental data indicative of a three-dimensional sub-gingival dental anatomy of patient 101. Digital image 300 is representative of volumetric dental data acquired from a CBCT scan of inferior portion of a skull 302 of patient 101, including a maxilla 304 and a mandible 306. The terms image and imaging as it is used herein is not limited to optical imaging but includes imaging of dental anatomies that are hidden from view. Digital image 300 represents a first subset 308 of sub-gingival dental data indicative of a three-dimensional sub-gingival dental anatomy of patient 101 and a second subset 310 of sub-gingival dental data indicative of a three-dimensional sub-gingival dental anatomy of patient 101. Similar to digital image 200, soft tissues have been filtered out, so only hard tissues are illustrated. First subset 308 includes crowns 312 of teeth of maxilla 304 and mandible 306. For example, first subset 308 may include tissues containing enamel, dentin, and cementum. Second subset 310 includes bone 314 of maxilla 304 and mandible 306. For example, second subset 310 may include tissues containing cortical bone and alveolar bone. Areas indicated by the dashed lines may include roots of the teeth, e.g., roots 316, where first subset 308 and second subset 310 overlap. Each of first subset 308 and second subset 310 may include a plurality of triangular vertices defining a mesh. In some examples, the mesh may be represented by other points, lines, and/or planes in a three-dimensional space, such as, for example, quadrilateral or hexagonal meshes, Bézier surfaces, Non-Uniform Rational Basis Spline (NURBS) surfaces, parametric solids, or other surface representations. In some examples, there may be a small gap between roots 316 and the alveolar bone 314 where the periodontal ligaments have been filtered out. In some examples, the alveolus of each tooth (e.g., the socket in the alveolar bone) may be capped-off to create a continuous surface over the occlusal side of the alveolar process. In this way, by using first subset 308 and second subset 310, crowns 312 may be segmented from bone 314 and roots 316.

Second imaging device 108, as illustrated in FIG. 1, may be configured to acquire digital image data including superficial dental data indicative of a three-dimensional superficial dental anatomy of patient 101. For example, second imaging device 108 may include an intra-oral scanner or imaging device configured to produce optical impressions of dental anatomy. Superficial dental anatomies include an anatomy of teeth of a patient above the gingiva and the gingiva, such as surface contours of the teeth, spacing of the teeth, and surface contours of the gingiva. In some examples, second imaging device 108 may be configured to scan teeth of patient 101, a physical impression of teeth of patient 101, or both. In examples in which second imaging device 108 is configured to scan a physical impression of teeth of patient 101, second imaging device 108 may include, for example, a CT scanner, a LASER scanner, a structured light scanner, 3D photogrammetry scanner, or the like.

Figure 4:
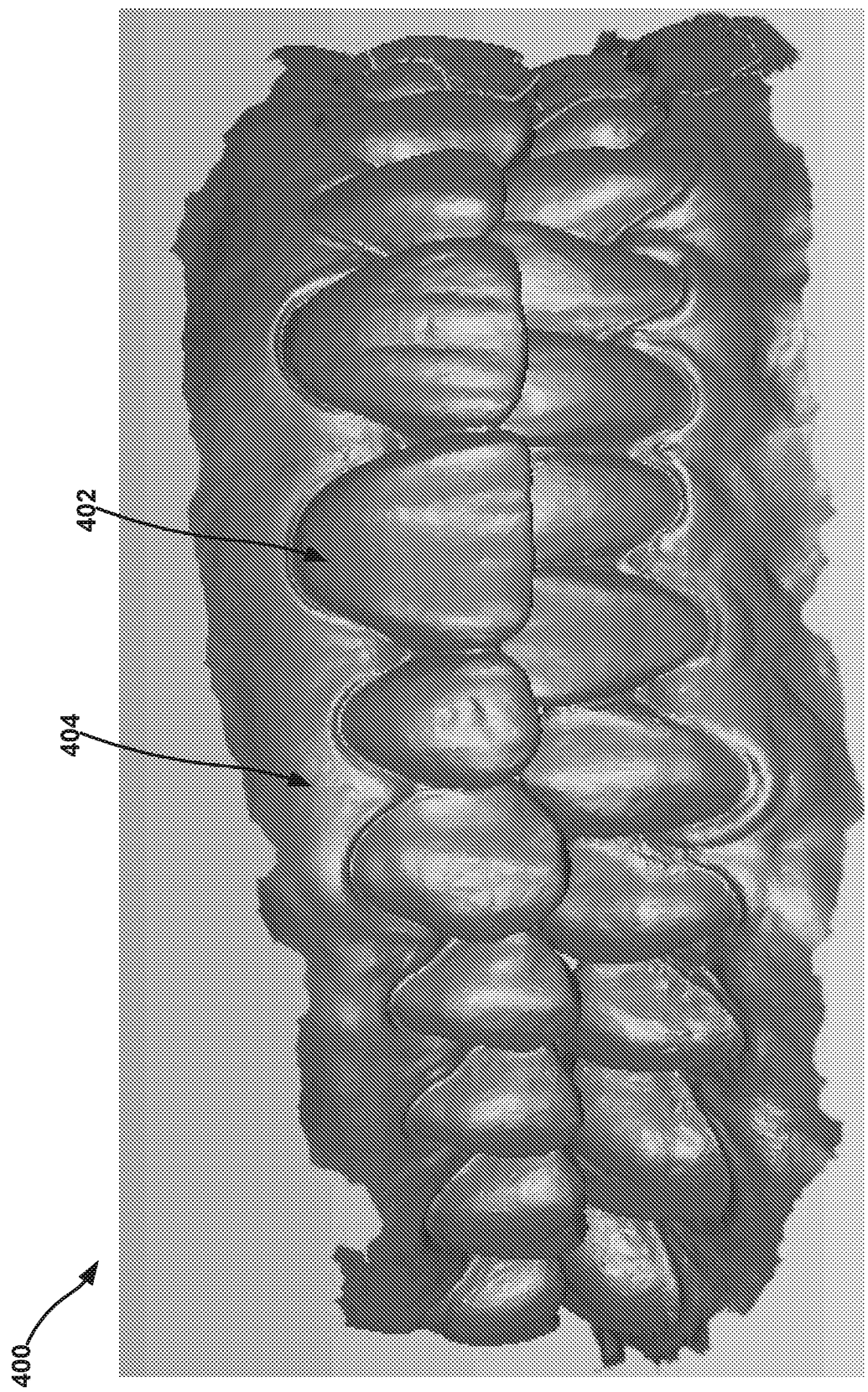
FIG. 4 illustrates an example digital image generated using superficial dental data indicative of a three-dimensional superficial dental anatomy of a patient.

FIG. 4 illustrates an example digital image 400 generated using superficial dental data indicative of a three-dimensional superficial dental anatomy of patient 101. Digital image 400 is representative of superficial dental data acquired from an intra-oral scan of crowns 402 of the teeth and gingiva 404 of patient 101. In some examples, second imaging device 108 may be configured to generate superficial dental data that includes triangular vertices defining a mesh representing optically visible surfaces of at least a portion of a maxillary arch of patient 101 or a mandibular arch of patient 101. In some examples, the mesh may be represented by other points, lines, and/or planes in a three-dimensional space, such as, for example, quadrilateral or hexagonal meshes, Bézier surfaces, Non-Uniform Rational Basis Spline (NURBS) surfaces, parametric solids, or other surface representations. The optically visible surfaces may include, for example, natural tooth crowns (e.g., enamel), artificial crowns, bridges, implants, orthodontic appliances (e.g., brackets, buttons, hooks, bands, splints, or the like), or temporary anchorage devices (mini-screws).

Image processing module 118 includes image data acquisition module 124, image data conditioning module 126, segmentation module 128, transformation module 130, image generation module 132, and image output module 134. Image data acquisition module 124, image data conditioning module 126, segmentation module 128, transformation module 130, image generation module 132, and image output module 134 may be implemented in various ways. For example, one or more of image data acquisition module 124, image conditioning module 126, segmentation module 128, transformation module 130, image generation module 132, and image output module 134 may be implemented as an application executed by processing circuitry 110 or as part of a hardware unit of computing device 102. Functions performed by one or more of image data acquisition module 124, image data conditioning module 126, segmentation module 128, transformation module 130, image generation module 132, and image output module 134 are explained below with reference to the example flow diagrams illustrated in FIGS. 5-14.

Figure 5:
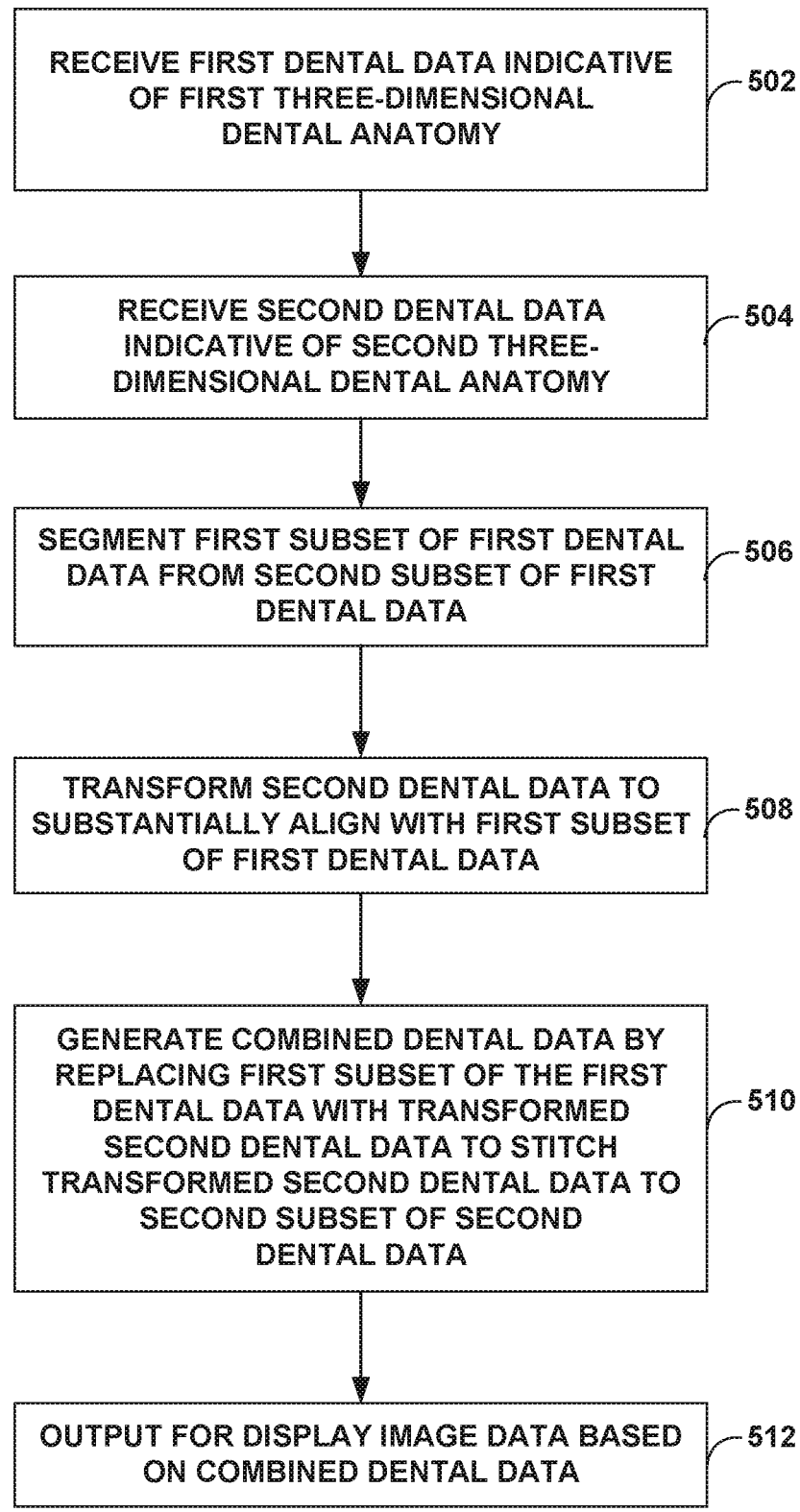
FIG. 5 is a flow diagram of an example technique for combining dental anatomy data from two or more different imaging devices.

FIG. 5 is a flow diagram of an example technique for combining dental anatomy data from two or more different imaging devices. Although the technique of FIG. 5 will be described with respect to system 100 of FIG. 1, in other examples, the technique of FIG. 5 may be performed using a different system. Additionally, system 100 may perform other techniques for combining dental anatomy data from two or more different imaging devices.

The technique illustrated in FIG. 5 includes receiving, by computing device 102, e.g., image data acquisition module 124, first dental data indicative of a first three-dimensional dental anatomy of a patient (502). The technique also includes receiving, by computing device 102, e.g., image data acquisition module 124, second dental data indicative of a second three-dimensional dental anatomy of the patient (504). As discussed above, first dental data may be acquired from first imaging device 106 and second dental data may be acquired from second imaging device 108.

After receiving the first dental data, the technique illustrated in FIG. 5 includes segmenting, by computing device 102, e.g., segmentation module 128, a first subset of the first dental data from a second subset of the first dental data (506). For example, as discussed above in reference to FIG. 3, the first subset of volumetric dental data may be representative of crowns 312. The second subset of the volumetric dental data representative of roots 316. In some examples, the first subset of the volumetric dental data may be indicative of a first spatial orientation of crowns 312. In some examples, the second subset of the volumetric dental data may be indicative of a spatial orientation of roots 316.

In some examples, at least a portion of the second dental data corresponds to the first subset of the first dental data. For example, as discussed above in reference to FIG. 4, second dental data may include crowns 402. Crowns 402 may correspond to crowns 312 of the first subset of the first dental data. By segmenting the first subset of the first dental data from a second subset of the first dental data, computing device 102 may define a sub-gingival portion and a superficial portion of the first dental data.

After segmenting the first dental data, the technique illustrated in FIG. 5 includes transforming, by computing device 102, e.g., transformation module 130, the corresponding portion of the second dental data to substantially align with the first subset of the first dental data. Transforming of the second dental data may include using any suitable transform. For example, a suitable transform may be configured to transform the second dental data indicative of a spatial orientation of crowns 402 to substantially align with the first subset of the first dental data indicative of a spatial orientation of crowns 312. With respect to alignment of an entire dental arch, substantially aligns may include, for example, aligning dental features of two respective scans within a range from about 2 millimeters to about 3 millimeters of one another, such as within about 0.25 millimeters. With respect to alignment of segments of a dental arch, substantially aligns may include aligning dental features of two respective scans within about 100 microns. With respect to alignment individual teeth or pairs of teeth, substantially aligns may include aligning dental features of two respective scans within about 25 microns to about 50 microns. In some examples, substantial alignment may include an alignment at or near the pixel or voxel resolution of the scanners, such that substantially aligns may be is based on statistical averages of many data points, such as computed centroids.

After transforming the second dental data, the technique illustrated in FIG. 5 includes generating, by computing device 102, e.g., image generation module 132, combined dental data by replacing the first subset of the first dental data with the transformed corresponding portion of the second dental data to stitch the transformed second dental data to the second subset of the first dental data. For example, generating the combined dental data may include replacing crowns 312 with the transformed corresponding portion of crowns 402 to stitch the transformed crowns 402 to bone 314 and/or roots 316.

Figure 6:
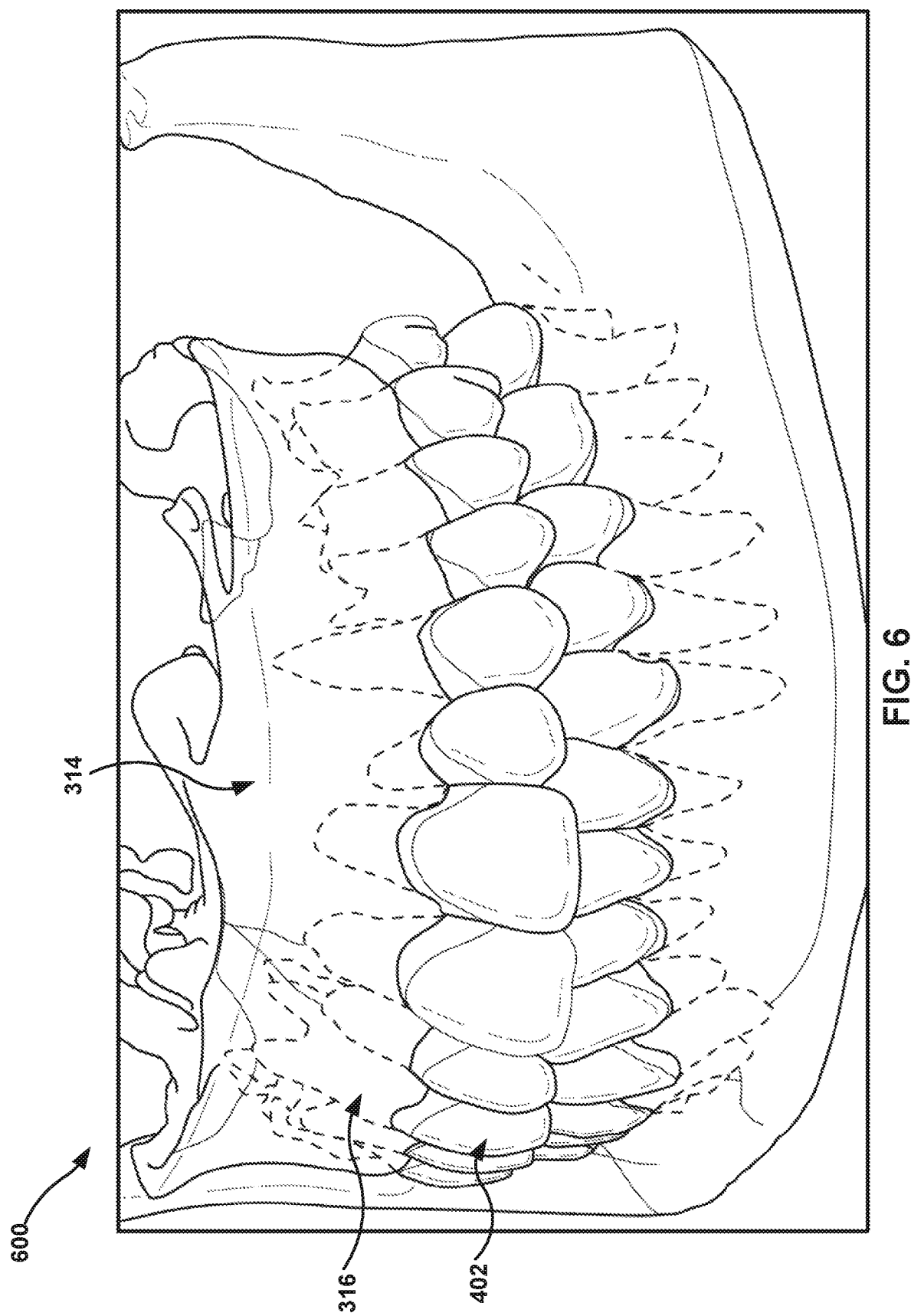
FIG. 6 illustrates an example digital image representative of combined dental data including the transformed corresponding portion of crowns of the superficial dental data stitched to bone and roots of the volumetric dental data.

After generating the combined dental data, the technique illustrated in FIG. 5 includes outputting, by computing device 102, e.g., image output module 134, and for display, e.g., user interface 114, image data based on the combined dental data (512). For example, FIG. 6 illustrates an example digital image 600 representative of combined dental data including the transformed corresponding portion of crowns 402 of the superficial dental data stitched to bone 314 and roots 316 of the volumetric dental data. In some examples, outputting may include outputting the combined dental data to a clinic or manufacturing facility for preparation of a dental appliance, such as a clear tray aligner, prosthetic, or the like.

Aspects of the technique in FIG. 5 can be used in conjunction with a removable restorative dental appliance to design the removable dental appliance around parts of the removable restorative dental appliance. In at least one embodiment, the first three-dimensional dental anatomy includes a removable restorative dental appliance worn by the patient, wherein the removable restorative dental appliance is not being worn by the patient in the second three-dimensional dental anatomy, or vice versa. In at least one embodiment, wherein the first subset of the first dental data includes volumetric dental data of the removable restorative dental appliance and the second subset of the first dental data includes volumetric dental data of a dentition of a patient.

Figure 17:
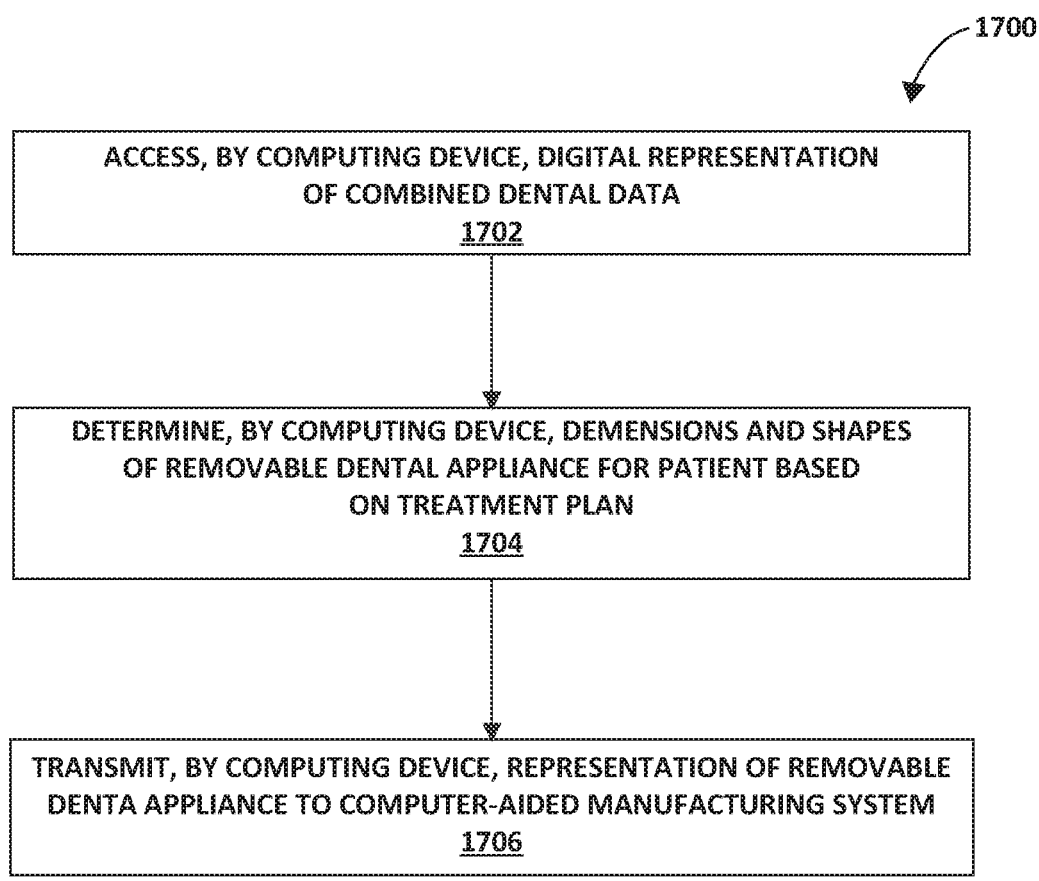
FIG. 17 is a flow diagram illustrating an example technique of transforming dental anatomy data.

FIG. 17 illustrates a flow diagram of a method 1700 for using the combined dental data from a removable restorative dental appliance. The method 1700 can be associated with the flow diagram in FIG. 5. For example, the block 1702 can continue after block 510. In at least one embodiment, the method 1700 can be related to designing a removable dental appliance around a pontic of a removable restorative dental appliance such that the pontic is not used as an anchor for the removable dental appliance. Aspects of method 1700 can be conducted at a manufacturing facility for construction of set of removable dental appliance.

In block 1702, the computing device 102 can receive a digital representation of combined dental (e.g., as obtained by block 510). The combined dental data can be accessed by the computing device 102 in any manner such as being transmitted from another computing device or accessing a local cache within the computing device 102. For example, computing device 102 at manufacturing facility receives digital dental anatomy data including initial positions of one or more teeth of the patient and prescription data from clinic. Alternatively, computing device 102 may retrieve the information from a database located within or otherwise accessible by computing device 102. A trained user associated with computing device 102 may interact with a computerized modeling environment running on computing device 102 to develop a treatment plan relative to the digital representation of the patient's tooth structure and generate prescription data 18, if clinic 14 has not already done so. In other examples, computing device 102 may automatically develop a treatment plan based solely on the patient's tooth structure and predefined design constraints.

In block 1704, the computing device 102 can determine dimensions and shapes of removable dental appliance for a patient based on a treatment plan. In at least one embodiment, the treatment plan excludes a segmented region (comprising at least a portion of the removable restorative dental appliance) from tooth position adjustments of adjacent teeth. For example, the computing device 102 can design the removable dental appliance such that a pontic from a removable restorative dental appliance experiences no force while changing the position of adjacent teeth to the pontic.

The removable dental appliance can include an appliance body configured to form at least partially surround a plurality of teeth of a dental arch of the patient. In at least one embodiment, the appliance body comprising a unitary material defining a shell shaped to receive at least one tooth of the patient. In at least one embodiment, the dimensions and shapes of the removable dental appliance comprise: a position, dimension, and shape of the shell.

Once computing device 102 receives patient's tooth structure, computing device 102 determines dimensions and shapes of a removable dental appliance for the patient in block 1704. The dimensions and shapes of the removable dental appliance are configured to reposition the one or more teeth of the patient from their initial positions to final positions when the removable dental appliance is worn by the patient. In the same or additional examples, computing device 102 determines dimensions and shapes of set of removable dental appliances 22 for the patient configured to be worn in series.

In some examples, determining dimensions and shapes of the removable dental appliance includes selecting, with computing device 102, the dimensions and shapes of the removable dental appliance according to a set of predefined design constraints. The set of predesigned design constraints may include one or more factors, including, but not limited to, at least one of a minimum and a maximum localized force applied to one or more of the surrounded teeth, at least one of a minimum and a maximum rotational force applied to one or more of the surrounded teeth, at least one of a minimum and a maximum translational force applied to one or more of the surrounded teeth, at least one of a minimum and a maximum total force applied to one or more of the surrounded teeth, and at least one of a minimum and a maximum stress or strain applied to the removable dental appliance, when the removable dental appliance is worn by the patient and the surrounded teeth are in their initial positions.

Computing device 102 may use finite element analysis (FEA) techniques to analyze forces on the teeth of the patient as well as the removable dental appliance during the determination of the dimensions and shapes of the removable dental appliance. For example, computing device 102 may apply FEA to a solid model of the teeth of the patient as the modeled teeth move from their initial positions to their final positions representing a treatment including an ordered set of removable dental appliances. Computing device 102 may use FEA to select the appropriate removable dental appliance to apply the desired forces on the teeth. In addition, computing device 102 may use a virtual articulator to determine contact points between the teeth throughout the movement of the modeled teeth during the treatment. Computing device 102 may further include occlusal contact forces, such as interdigitation forces, in the FEA forces analysis in combination with forces from the removable dental appliance during the design of dental appliances in an ordered set of removable dental appliances. Computing device 102 may further determine an order in which teeth are to be moved to optimize the application of forces, reduce treatment time, improve patient comfort, or the like. Computing device 102 may further determine an overcorrection of the dentition to account for relapse after treatment is ended.

In some examples, determining dimensions and shapes of removable dental appliance includes selecting, with computing device 102 thicknesses of the appliance body or shells, positioning members flexural regions to provide a stiffness suitable to reposition the one or more teeth of the patient from their initial positions to final positions when removable dental appliance is worn by the patient. In some examples, the selected thickness may range between about 0.10 millimeters and about 2.0 millimeters, such as between about 0.2 and about 1.0 millimeters or between about 0.3 and about 0.75 millimeters. In some examples, computing device 102 may further select a material of the removable dental appliance according to the predefined design constraints.

The dimensions and shapes of a removable dental appliance for the patient may be presented to a user via image output module of computing device 102 as in block 512. In examples in which dimensions and shapes of the removable dental appliance are presented to a user, the user may have the opportunity to adjust the design constraints or directly adjust the dimensions and shapes of the removable dental appliance before the design data is sent to computer-aided manufacturing system 20. In some examples, the dimensions and shapes of the removable dental appliance may be presented to a user by computing device 102 directly as the removable dental appliance is manufactured by computer-aided manufacturing system 20. For example, computing device 102 may send a digital model of the removable dental appliance to computer-aided manufacturing system 20, and computer-aided manufacturing system 20 manufactures the removable dental appliance according to the digital model from computing device 102.

However, even in examples where the dimensions and shapes of a removable dental appliance for the patient may be presented to a user via user interface of computing device 102, following user approval, computing device 102 sends a digital model of the removable dental appliance to computer-aided manufacturing system 20 in block 1706, and computer-aided manufacturing system 20 manufactures the removable dental appliance according to the digital model from computing device 102.

In some examples, computer-aided manufacturing system 20 may include a 3D printer. Forming the appliance body may include printing at least one of spring members, attachments, shells, positioning members, flexural regions, stress reduction regions, and biased portions with the 3D printer. In other examples, forming the appliance body may include printing representations of the teeth of the patient with the 3D printer, thermoforming the appliance body over the representations of the teeth, and trimming excess material to form at least one of spring members, attachments, shells, positioning members, flexural regions, stress reduction regions, and biased portions. The representations of the teeth of the patient may include raised surfaces to facilitate forming the at least one of spring members, attachments, shells, positioning members, flexural regions, stress reduction regions, and biased portions in the thermoformed and trimmed appliance body.

The techniques of method 1700 may be applied to design and manufacture of each of an ordered set of removable dental appliances 22. For example, each removable dental appliance in the ordered set of removable dental appliances 22 may be configured to incrementally reposition the teeth of the patient. In this manner, the ordered set of removable dental appliances 22 may be configured to reposition the teeth of the patient to a greater degree than any one of the removable dental appliances within the set of the removable dental appliances 22. Such an ordered set of removable dental appliances 22 may specifically be configured to incrementally reposition the one or more teeth of the patient from their initial positions to final positions as the removable dental appliances of the ordered set of removable dental appliances 22 for the patient are worn sequentially by the patient.

Figure 7:
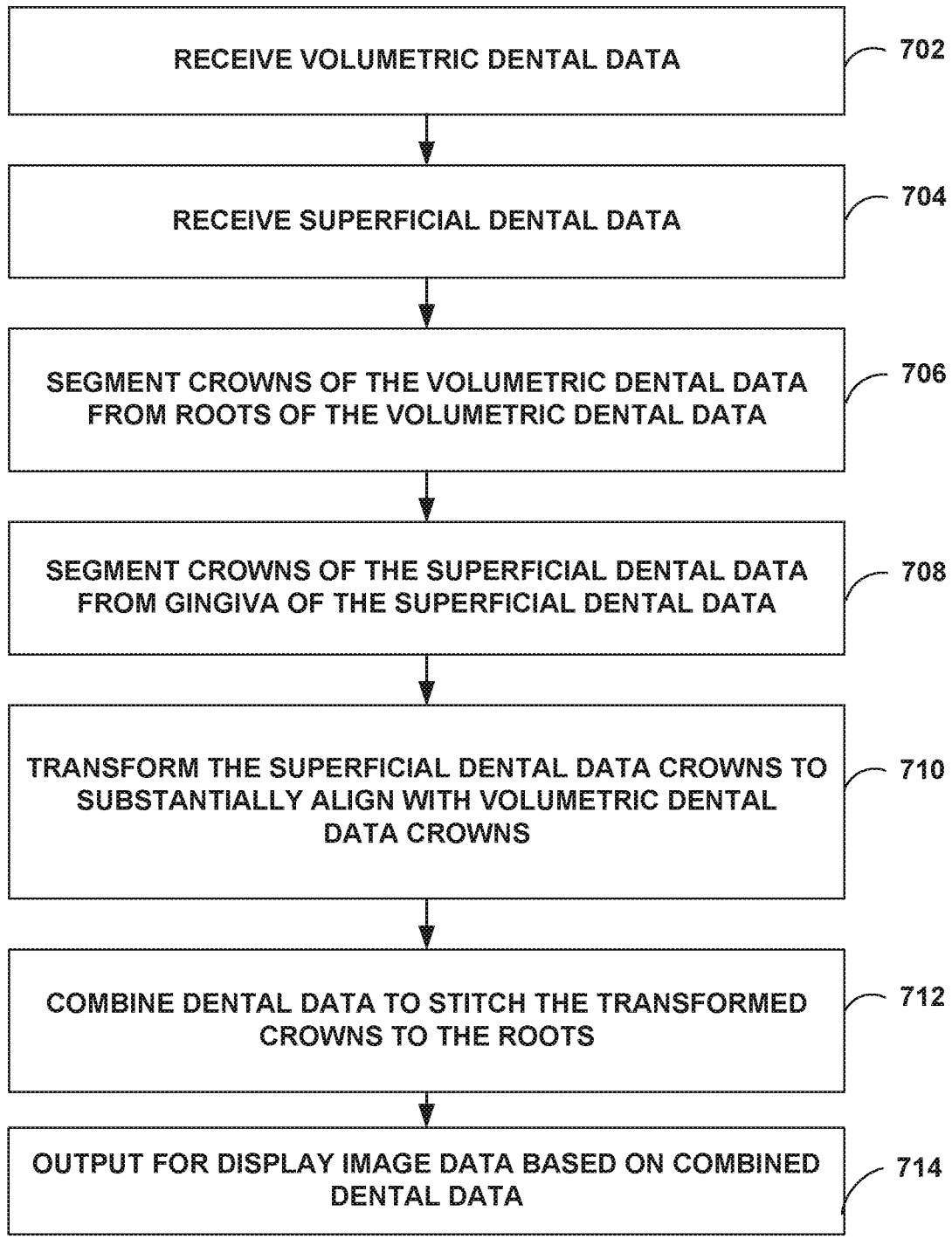
FIG. 7 is a flow diagram of an example technique for combining dental anatomy data from two or more different imaging devices.

FIG. 7 is a flow diagram of an example technique for combining dental anatomy data from two or more different imaging devices. Although the technique of FIG. 7 will be described with respect to system 100 of FIG. 1, in other examples, the technique of FIG. 7 may be performed using a different system. Additionally, system 100 may perform other techniques for combining dental anatomy data from two or more different imaging devices.

The technique illustrated in FIG. 7 includes receiving, by computing device 102, e.g., image data acquisition module 124, volumetric dental data indicative of a three-dimensional sub-gingival dental anatomy of patient 101 (702). For example, volumetric dental data may include data representative of digital image 300, as illustrated in FIG. 3. The technique also includes receiving, by computing device 102, e.g., image data acquisition module 124, superficial dental data indicative of a three-dimensional superficial dental anatomy of patient 101 (704). For example, superficial dental data may include dental data representative of digital image 400, as illustrated in FIG. 4. Although not illustrated in FIG. 7, the technique may include controlling first imaging device 106 to acquire the volumetric dental data, controlling second imaging device 108 to acquire the superficial dental data, communicating with a network to retrieve the volumetric dental data or the superficial dental data, or a combination thereof.

After receiving the volumetric dental data, the technique illustrated in FIG. 7 includes segmenting, by computing device 102, e.g., segmentation module 128, a first subset of the volumetric dental data representative of crowns of teeth of the patient from a second subset of the volumetric dental data representative of roots of the teeth (706). For example, as discussed above in reference to FIG. 3, the first subset of the volumetric dental data may be representative of crowns 312. The second subset of the volumetric dental data may be representative of roots 316. In some examples, the first subset of the volumetric dental data may be indicative of a first spatial orientation of crowns 312. In some examples, the second subset of the volumetric dental data may be indicative of a spatial orientation of roots 316. By segmenting the first subset of the volumetric dental data from a second subset of the volumetric dental data, computing device 102 may define a sub-gingival portion (e.g., roots 316) and a superficial portion of the volumetric dental data (e.g., crowns 312).

In some examples, segmenting the first subset of the volumetric dental data from the second subset of the volumetric dental data may include segmenting, by computing device 102, e.g., segmentation module 128, the first spatial orientation of crowns 312 from the spatial orientation of roots 316 by combining points of a point cloud indicative of at least one of enamel, dentin, cementum, or restorative materials and determining, by computing device 102, e.g., segmentation module 128, a triangular vertex mesh that defines the outer surface of the combined points. Determining the triangular vertex mesh may include wrapping the combined points of the point cloud in the triangular vertex mesh.

After receiving the superficial dental data, the technique illustrated in FIG. 7 includes, segmenting, by computing device 102, e.g., segmentation module 128, a first subset of the superficial dental data representative of the crowns from a second subset of the superficial dental data representative of the gingiva of the patient (708). For example, as discussed above in reference to FIG. 4, the first subset of the superficial dental data may be representative of crowns 402. The second subset of the superficial dental data may be representative of gingiva 404. In some examples, the first subset of the superficial dental data may be indicative of a second spatial orientation of crowns 402. In some examples, the second subset of the superficial dental data may be indicative of a spatial orientation of gingiva 404. By segmenting the first subset of the superficial dental data from a second subset of the superficial dental data, computing device 102 may define a portion of the superficial dental data that corresponds to the superficial portion of the volumetric dental data. For example, crowns 402, as discussed above in reference to FIG. 4, may correspond to crowns 312, as discussed above in reference to FIG. 4.

Although not illustrated in FIG. 7, in some examples, the technique may include defining, by computing device 102, a first group that includes a portion of the first subset of the volumetric dental data and the second subset of the volumetric dental data. The technique also may include defining, by computing device 102, a second group that includes a portion of the first subset of the superficial dental data. The portion of the first subset of the superficial dental data may correspond to the portion of the first subset of the volumetric dental data. For example, the first group may include crowns of a maxillary arch or a mandibular arch of the volumetric dental data and corresponding roots of the maxillary arch or the mandibular arch of the volumetric dental data, and the second group may include crowns of the maxillary arch or the mandibular arch of the superficial dental data. In this sense, the first and second groups may be considered respective arch-shaped objects.

In some examples, the first group may include a plurality of first groups and the second group may include a plurality of second groups. Each first group of the plurality of first groups may include at least two crowns of the first subset of the volumetric dental data and at least two corresponding roots of the second subset of the volumetric dental data. Each second group of the plurality of second groups may include at least two crowns of the first subset of the superficial dental data. Defining first groups and second groups may reduce the computational intensity or time to transform the superficial dental data.

After segmenting the first dental data, the technique illustrated in FIG. 7 includes transforming, by computing device 102, e.g., transformation module 130, the first subset of the superficial dental data indicative of the second spatial orientation of the crowns such that the second spatial orientation of the crowns substantially aligns with the first spatial orientation of the crowns (710). Transforming of the first subset of the superficial dental data may include using any suitable transform. For example, transforming (710) may include transforming, by computing device 102, e.g., transformation module 130, the first subset of the superficial dental data indicative of the second spatial orientation of crowns 402 such that the second spatial orientation of crowns 402 substantially aligns with the first spatial orientation of crowns 312. In some examples, transforming (710)

may include applying a plurality of linear transforms to data representative of different segments (or portions) of a dental arch, a continuous transform function that varies along a path that describes the arch to data representative of the dental arch, or both. In some examples, different segments of the dental arch may be as small as individual vertices in a triangular mesh representative of the dental arch.

After transforming the second dental data, the technique illustrated in FIG. 7 includes generating, by computing device 102, e.g., image generation module 132, combined dental data by replacing the first subset of the sub-gingival data indicative of the first spatial orientation of the crowns with the transformed first subset of the superficial dental data indicative of the second spatial orientation of the crowns to stitch the transformed first subset of the superficial dental data indicative of the second spatial orientation of the crowns to the second subset of the volumetric dental data representative of the roots (712). For example, generating the combined dental data may include replacing crowns 312 with the transformed corresponding portion of crowns 402 to stitch the transformed crowns 402 to bone 314 and/or roots 316.

Figure 8A:
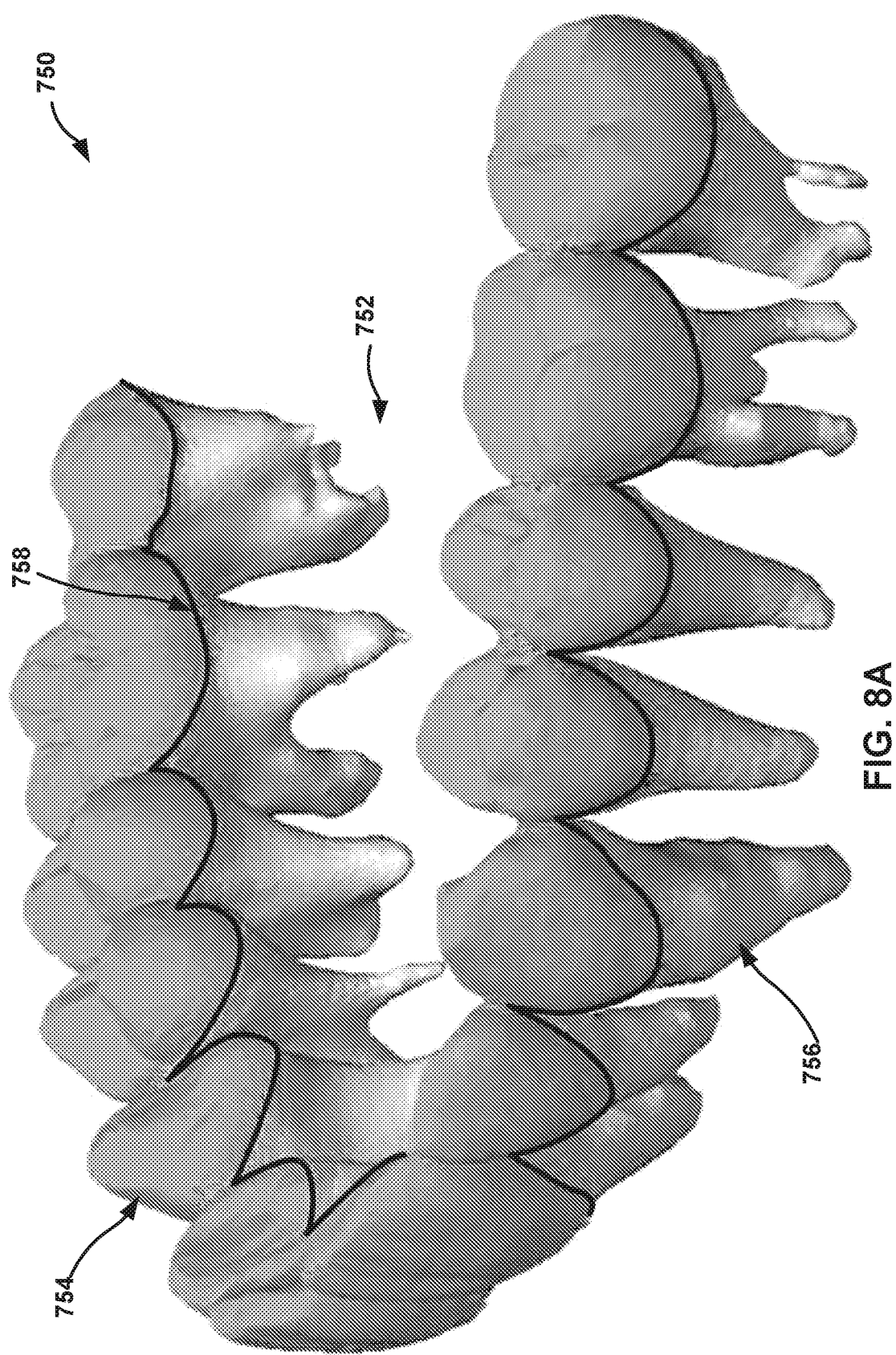
FIGS. 8A and 8B illustrate an example digital image representative of combined dental data including the transformed corresponding portion of crowns of superficial dental data stitched to roots of volumetric dental data.
Figure 8B:
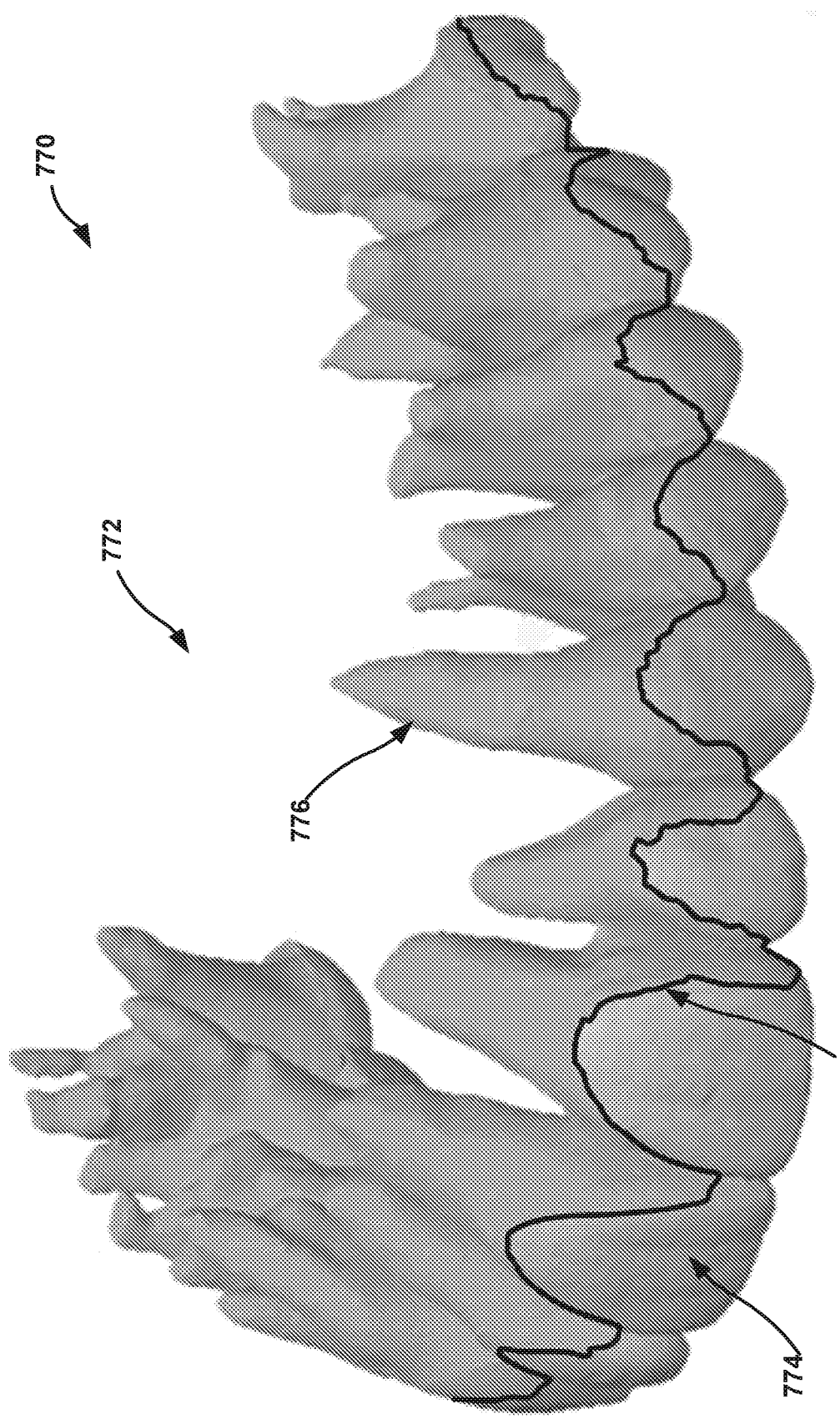

After generating the combined dental data, the technique illustrated in FIG. 7 includes outputting, by computing device 102, e.g., image output module 134, and for display, e.g., user interface 114, image data based on the combined dental data (714). For example, FIGS. 8A and 8B illustrate an example digital images representative of combined dental data including the transformed corresponding portion of crowns of superficial dental data stitched to roots of volumetric dental data. FIG. 8A illustrates dental image 750 representative of a mandibular arch 752 including crowns 754 and roots 756, which meet at smooth and continuous interface 758. Interface 758 does not include any significant step from crowns 754 to roots 756. FIG. 8B illustrates dental image 770 representative of a maxillary arch 772 including crowns 774 and roots 776, which meet at smooth and continuous interface 778. Interface 778 does not include any significant step (visible discontinuity) from crowns 774 to roots 776.

Figure 9A:
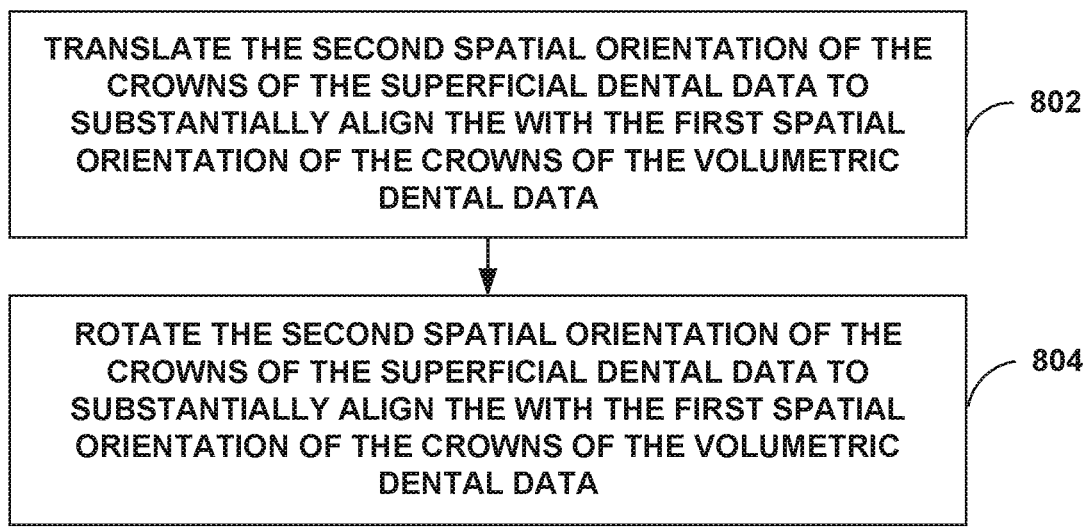
FIGS. 9A-9C are diagrams illustrating an example technique of transforming dental anatomy data.
Figure 9B:
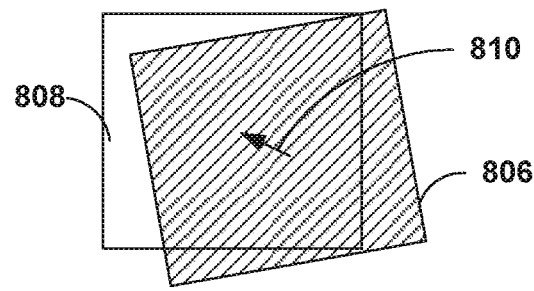
Figure 9C:
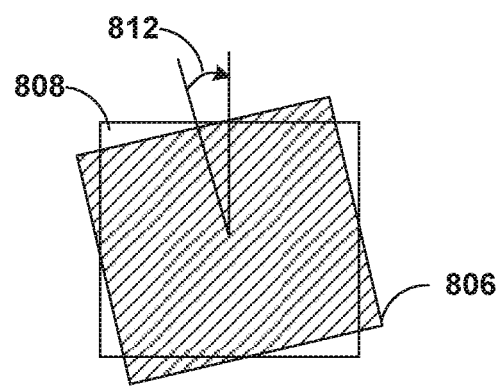

As discussed in further detail below, in some examples, transforming (710) may include one or more of the techniques illustrated in reference to FIGS. 9A-15. FIGS. 9A-9C are diagrams illustrating an example technique of transforming dental anatomy data. Although the technique of FIGS. 9A-9C will be described with respect to system 100 of FIG. 1, in other examples, the technique of FIGS. 9A-9C may be performed using a different system. Additionally, system 100 may perform other techniques for transforming dental anatomy data.

The technique illustrated in the flow diagram of FIG. 9A may include translating, by computing device 102, e.g., transformation module 130, the second spatial orientation of the crowns of the superficial dental data to substantially align with the first spatial orientation of the crowns of the volumetric dental data (802). For example, as illustrated in FIG. 9B, superficial dental data representative of a spatial orientation of crown 806 may be translated (e.g., translation 810) to substantially align with volumetric dental data representative of a spatial orientation of crown 808. Although illustrated as a two-dimensional translation, the translation may be in three-dimensions. The translation may include both position and orientation translation components. In some examples, the translation may include a scaling component. The technique illustrated in FIG. 9A may include rotating, by computing device 102, e.g., transformation module 130, the second spatial orientation of the crowns of the superficial dental data to substantially align the with the first spatial orientation of the crowns of the volumetric dental data (804). For example, as illustrated in FIG. 9C, superficial dental data representative of a spatial orientation of crown 806 may be rotated (e.g., rotation 812) to substantially align with volumetric dental data representative of a spatial orientation of crown 808. Although illustrated as a rotation along a single axis, the rotation may be relative to two or more axes.

In some examples, translating (802) and or rotating (804) as a single, monolithic object, may define a "best-fit registration" of the second spatial orientation of the crowns of the superficial dental data to the first spatial orientation of the crowns of the volumetric dental data. In some examples, best-fit registering the second spatial orientation of the crowns of the superficial dental data (e.g., as a single, monolithic object) to the first spatial orientation of the crowns of the volumetric dental data (e.g., as a single, monolithic object) may result in a slight misfit due to distortion in the first spatial orientation of the crowns of the volumetric dental data.

FIGS. 10A and 10B are example images 900A and 900B representing a best-fit registration of a crown 902 (e.g., a crown of crowns 402) to a tooth root 904 (e.g., a root of roots 316). FIG. 10B illustrates a 90-degree rotation of the view illustrated in FIG. 10A. As illustrated in FIGS. 10A and 10B, best-fit alignment may result in a step 906 in position between crown 902 and corresponding root 904. Step 906 may represent a misalignment in translation and/or rotation (e.g., position error and orientation error, respectively). In the example illustrated in FIGS. 10A and 10B, a magnitude of the position error is greater than a magnitude of the orientation error.

Figure 11A:
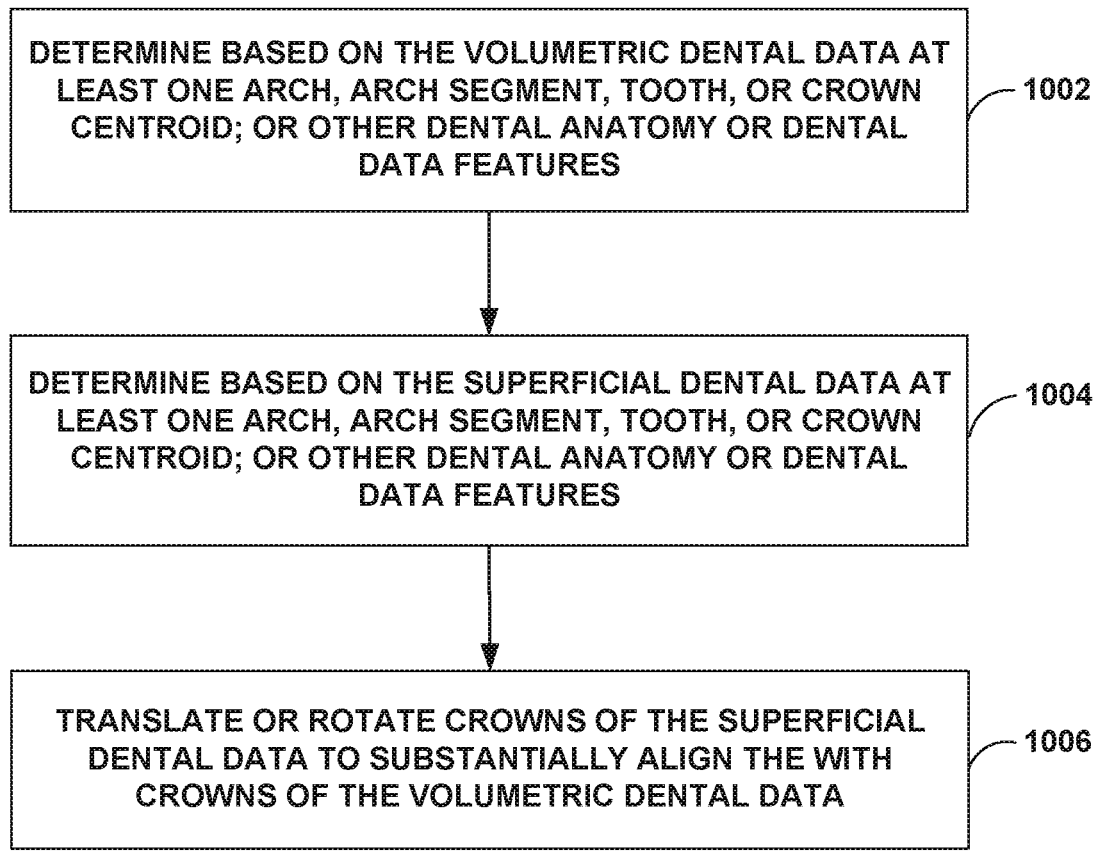
FIGS. 11A-11C are diagrams illustrating an example technique of transforming dental anatomy data using centroids.
Figure 11B:
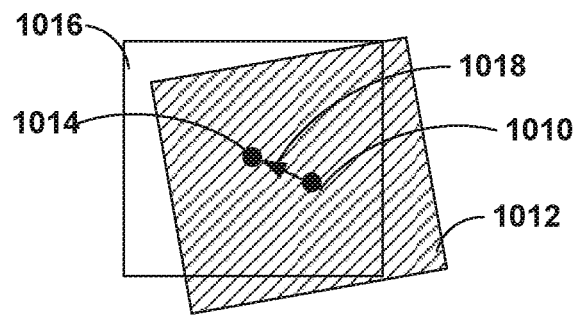
Figure 11C:
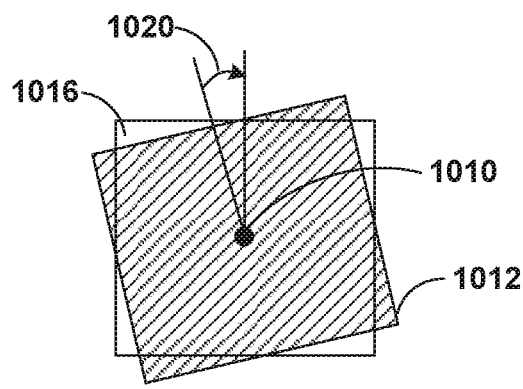

To reduce error from best-fit registration, centroids or other data features may be used to improve alignment via translation and/or rotation. FIGS. 11A-11C are diagrams illustrating an example technique of transforming dental anatomy data using centroids. Although the technique of FIG. 11 will be described with respect to system 100 of FIG. 1, in other examples, the technique of FIG. 11 may be performed using a different system. Additionally, system 100 may perform other techniques for transforming dental anatomy data.

The technique illustrated in FIG. 11A includes determining, by computing device 102, e.g., transformation module 130, based on the first spatial orientation of the crowns of the volumetric dental data, at least one of an arch centroid, one or more arch segment centroids, one or more tooth centroids, one or more crown centroids, one or more dental anatomical landmarks, one or more mesh vertices, one or more mesh triangles (1002). The technique illustrated in FIG. 11A includes determining, by computing device 102, e.g., transformation module 130, based on the second spatial orientation of the crowns of the superficial dental data, at least one of an arch centroid, one or more arch segment centroids, one or more tooth centroids, one or more crown centroids, one or more dental anatomical landmarks, one or more mesh vertices, one or more mesh triangles (1004). As used herein, centroids may include the geometric center of the triangular vertex mesh representing the surface of a respective feature of the dental anatomy or features of the dental anatomy data. Features of the dental anatomy may include an entire arch, a segment of the arch, individual crowns, other landmarks (e.g., implants, prosthetics, or natural dental anatomy features). Features of the dental anatomy data may include one or more coordinate sets representing one or more points on a mesh defining the three-dimensional shape of a feature of the dental anatomy.

The technique illustrated in FIG. 11A includes at least one of translating by modifying a position of or rotating, by computing device 102, e.g., transformation module 130, the at least one of an arch centroid, one or more arch segment centroids, one or more tooth centroids, one or more crown centroids, one or more dental anatomical landmarks, one or more mesh vertices, one or more mesh triangles of the second spatial orientation of the crowns of the superficial dental data in a three-dimensional space to substantially align with the at least one of an arch centroid, one or more arch segment centroids, one or more tooth centroids, one or more crown centroids, one or more dental anatomical landmarks, one or more mesh vertices, one or more mesh triangles of the first spatial orientation of the crowns of the volumetric dental data (1006).

For example, as illustrated in FIG. 11B, computing device 102, e.g., transformation module 130, may be configured to determine centroid 1010 of superficial dental data representative of a spatial orientation of crown 1012. Similarly, computing device 102, e.g., transformation module 130, may be configured to determine centroid 1014 of volumetric dental data representative of a spatial orientation of crown 1016. Computing device 102, e.g., transformation module 130, may be configured to determine a translation 1018 from centroid 1010 to centroid 1014, and then apply the determined translation to each triangular vertex of the mesh defining crown 1012. Although illustrated as a two-dimensional translation, it is understood that the translation may be in three-dimensions. As illustrated in FIG. 11C, computing device 102, e.g., transformation module 130, may be configured to determine a rotation 1020 of crown 1012, e.g., with centroid 1010 as the axis of rotation, to substantially align with crown 1016.

Although illustrated in FIG. 11C as a single rotation along a single axis, the rotation may be relative to two or more axes. FIGS. 12A-12D are diagrams illustrating an example technique of transforming dental anatomy data including a vertical rotation and a horizontal rotation. Although the technique of FIGS. 12A-12D will be described with respect to system 100 of FIG. 1, in other examples, the technique of FIGS. 12A-12D may be performed using a different system. Additionally, system 100 may perform other techniques for transforming dental anatomy data.

Figure 12A:
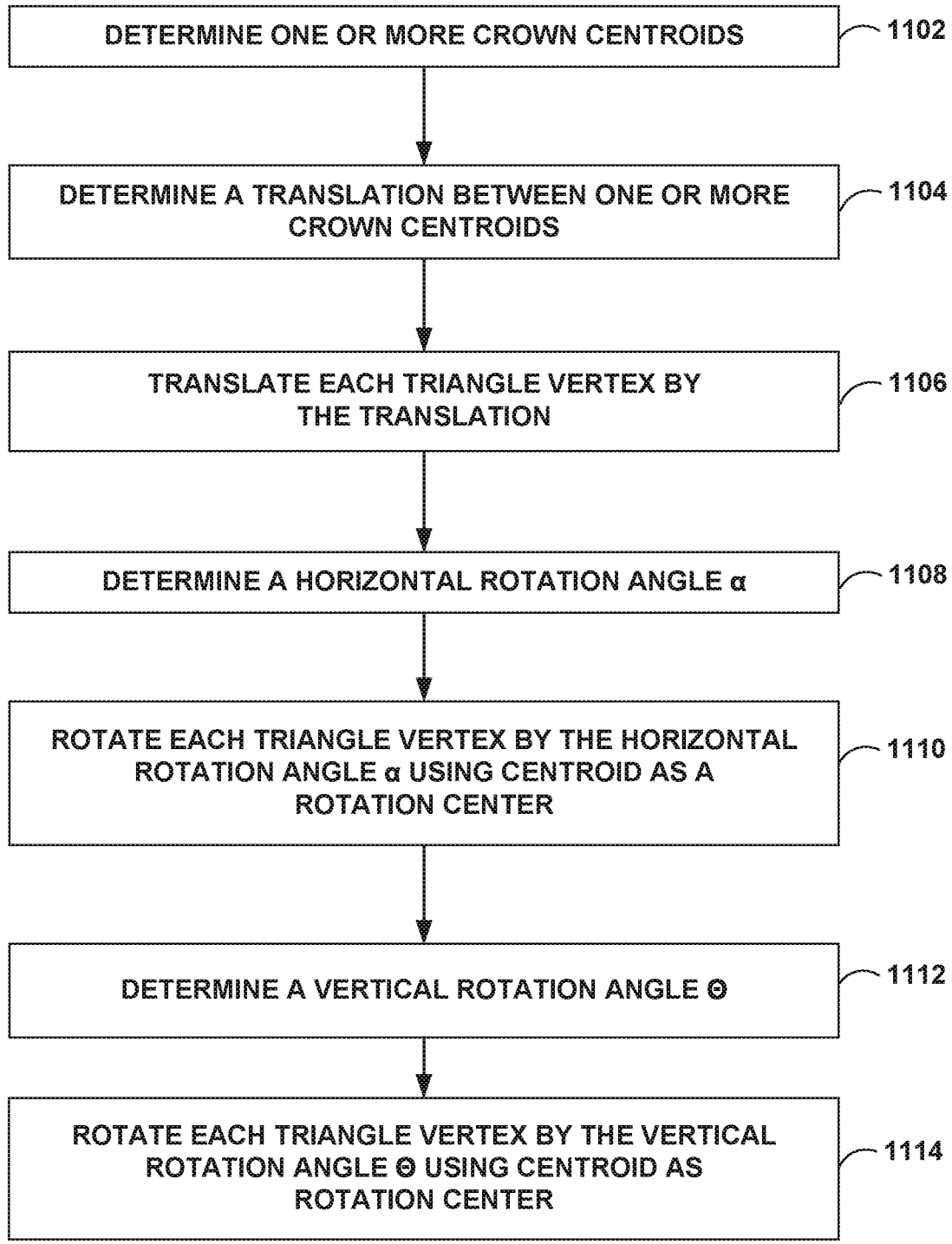
FIGS. 12A-12D are diagrams illustrating an example technique of transforming dental anatomy data including a vertical rotation and a horizontal rotation.
Figure 12B:
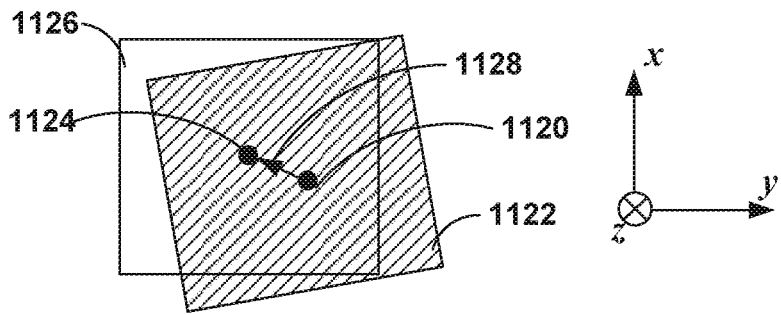

The technique illustrated in FIG. 12A includes determining, by computing device 102, e.g., transformation module 130, one or more crown centroids of the first spatial orientation of the crowns of the volumetric dental data and the second spatial orientation of the crowns of the superficial dental data (1102). The one or more centroids may include the geometric center of the triangular vertex mesh representing the surface of the crowns of the respective dental data. For example, as illustrated in FIG. 11B, centroid 1120 may include the arithmetic mean position of all the vertices of a mesh representing crown 1122 and centroid 1124 may include the arithmetic mean position of all the vertices of a mesh representing crown 1126. In this way, a respective centroid may be defined for each tooth of a dental arch of patient 101 represented by the respective volumetric or superficial dental data.

The technique illustrated in FIG. 12A includes determining, by computing device 102, e.g., transformation module 130, a translation between one or more crown centroids of the first spatial orientation of the crowns of the volumetric dental data and the corresponding one or more crown centroids of the second spatial orientation of the crowns of the superficial dental data (1104). The technique illustrated in FIG. 12A includes translating, by computing device 102, e.g., transformation module 130, each triangle vertex of a mesh defining the second spatial orientation of the crowns of the superficial dental data by the translation (1106). For example, as illustrated in FIG. 11B, computing device 102, e.g., transformation module 130, may be configured to determine a translation 1128 from centroid 1120 to centroid 1124, and then apply the determined translation to each triangular vertex of the mesh defining crown 1122. Although illustrated as a two-dimensional translation, the translation may be in three-dimensions. In this way, each tooth of the arch may be translated into an intermediate alignment with the corresponding tooth in the first spatial orientation of the crowns of the volumetric dental data.

Figure 12C:
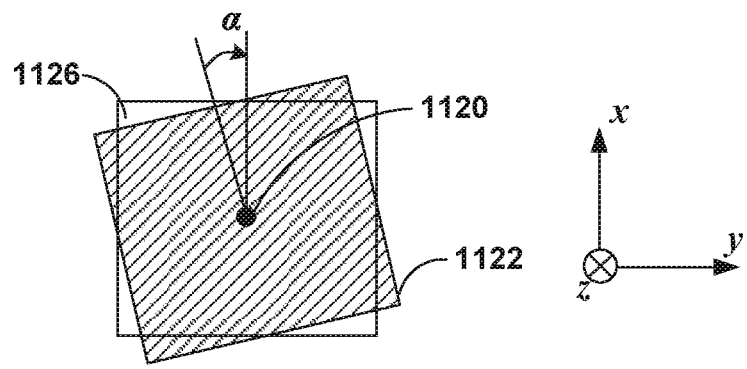
Figure 12D:
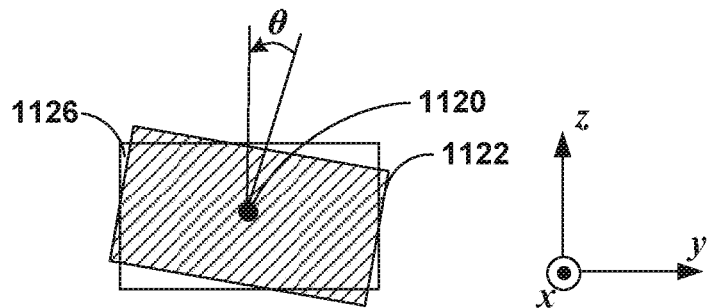

The technique illustrated in FIG. 12A includes determining, by computing device 102, e.g., transformation module 130, a horizontal rotation angle $\alpha$ between a first vector between a first crown and a second crown of the first spatial orientation of the crowns of the volumetric dental data and a second vector between a third crown and a fourth crown of the second spatial orientation of the crowns of the superficial dental data, where the first crown corresponds to the third crown and the second crown corresponds to the fourth crown (1108). The technique also includes rotating, by computing device 102, e.g., transformation module 130, each triangle vertex of the mesh defining the third crown by the horizontal rotation angle $\alpha$ using a centroid of the third crown as a rotation center (1110). For example, as illustrated in FIG. 12C, computing device 102, e.g., transformation module 130, may be configured to determine horizontal rotation angle $\alpha$ of crown 1122, and rotate crown 1122 about centroid 1120 as the axis of rotation to substantially align with crown 1126. In some examples, the first crown and second crown include mesial-distal adjacent teeth or, in the case of the mesial-most crown, crowns of the adjacent quadrant of the dental arch. Determination of the horizontal rotation may be repeated for each tooth of the arch.

The technique illustrated in FIG. 12 includes determining, by computing device 102, e.g., transformation module 130, a vertical rotation angle $\theta$ between a third vector between the first crown and a centroid of the first spatial orientation of the crowns of the volumetric dental data and a fourth vector between the third crown and a centroid of the second spatial orientation of the crowns of the superficial dental data (1112). The technique also includes rotating, by computing device 102, e.g., transformation module 130, each triangle vertex of the mesh defining the third crown by the vertical rotation angle $\theta$ using the centroid of the third crown as a rotation center (1114). For example, as illustrated in FIG. 12D, computing device 102, e.g., transformation module 130, may be configured to determine vertical rotation angle $\theta$ of crown 1122, and rotate crown 1122 about centroid 1120 as the axis of rotation to substantially align with crown 1126.

In some examples, transforming the second spatial orientation of the crowns of the superficial dental data may include repeating the horizontal rotation and the vertical rotation for each crown of the second spatial orientation of the crowns of the superficial dental data.

Figure 13:
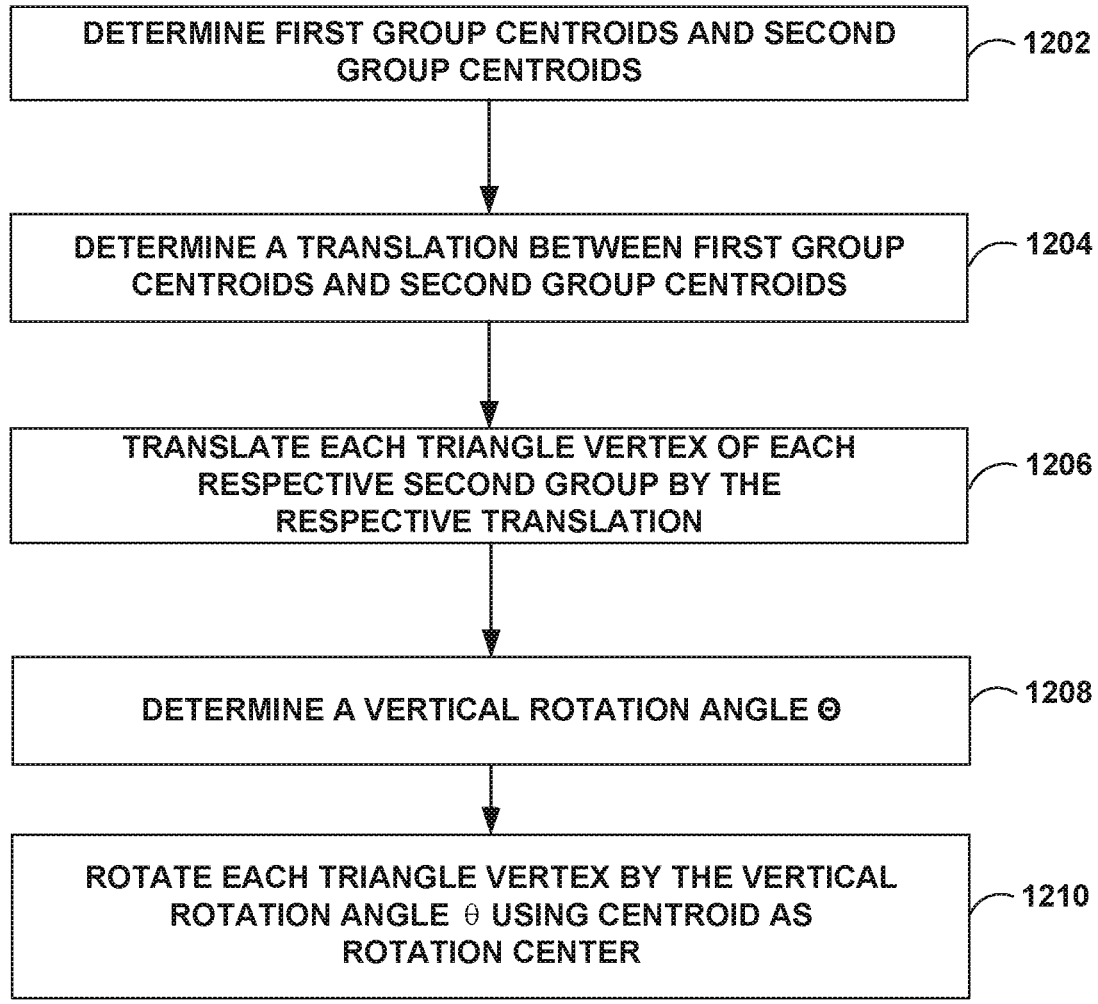
FIG. 13 is a flow diagram illustrating an example technique of transforming dental anatomy data.

FIG. 13 is a flow diagram of an example technique of transforming dental anatomy data. Although the technique of FIG. 13 will be described with respect to system 100 of FIG. 1, in other examples, the technique of FIG. 13 may be performed using a different system. Additionally, system 100 may perform other techniques for transforming dental anatomy data.

The technique illustrated in FIG. 13 includes determining, by computing device 102, e.g., transformation module 130, first centroids of each first group of the plurality of first groups and second centroids of each second group of the plurality of second groups (1202). For example, as discussed above, the volumetric dental data and superficial dental data may be subdivided into groups representing sections of a dental arch. Respective centroids include the geometric center of the triangular vertex mesh representing the surface of respective groups. Determining group centroids may reduce the computational intensity or time compared to determining centroids for each crown.

The technique illustrated in FIG. 13 includes determining, by computing device 102, e.g., transformation module 130, a translation between each first centroid and corresponding second centroid (1204). The technique illustrated in FIG. 13 includes translating, by computing device 102, e.g., transformation module 130, each triangle vertex of each mesh defining each second group of the plurality of second groups by the translation (1206). In this way, each group (e.g., each section of teeth of the arch) may be translated into an intermediate alignment with the corresponding group.

The technique illustrated in FIG. 13 includes determining, by computing device 102, e.g., transformation module 130, a vertical rotation angle θ between a first vector between a respective first centroid and a centroid of the plurality of first groups and a second vector between a respective second centroid and a centroid of the plurality of second groups (1208). The technique illustrated in FIG. 13 includes rotating, by computing device 102, e.g., transformation module 130, each triangle vertex of each mesh defining each second group of the plurality of second groups by the vertical rotation angle θ using the respective second centroid as a rotation center (1210). In some examples, transforming the second spatial orientation of the crowns of the superficial dental data may include repeating the vertical rotation for each second group of the plurality of second groups.

Figure 14:
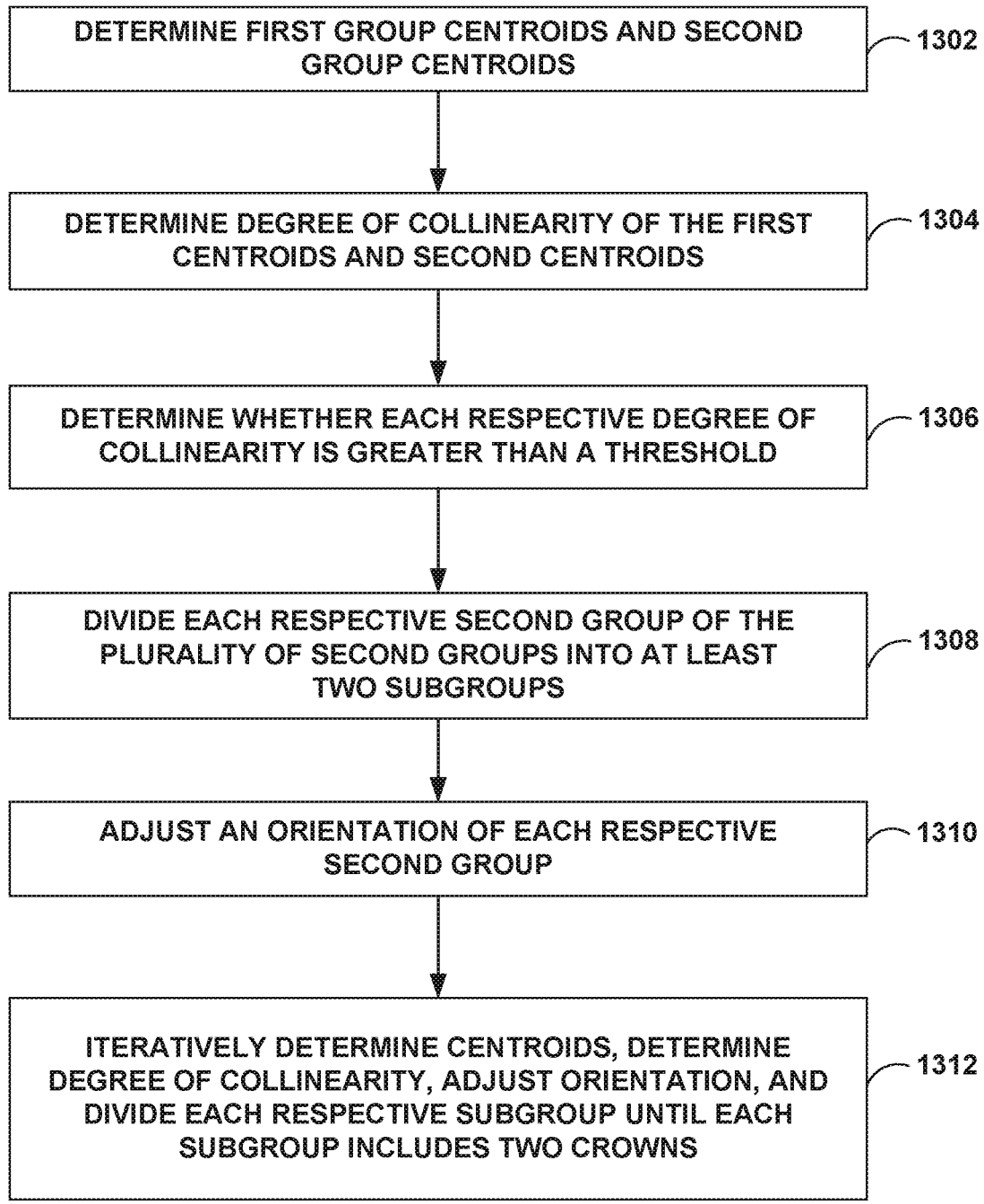
FIG. 14 is a flow diagram illustrating an example technique of transforming dental anatomy data.

FIG. 14 is a flow diagram of an example technique of transforming dental anatomy data. Although the technique of FIG. 14 will be described with respect to system 100 of FIG. 1, in other examples, the technique of FIG. 14 may be performed using a different system. Additionally, system 100 may perform other techniques for transforming dental anatomy data.

The technique illustrated in FIG. 14 includes determining, by computing device 102, e.g., transformation module 130, first centroids of each first group of the plurality of first groups and second centroids of each second group of the plurality of second groups (1302). Step 1302 may be the same or substantially similar to step 1202 discussed above.

The technique illustrated in FIG. 14 includes determining, by computing device 102, e.g., transformation module 130, a respective degree of collinearity of the first centroids and second centroids (1304). For example, each first centroid may be joined to adjacent first centroids by a first vector and each second centroid may be joined to adjacent second centroids by a second vector. Corresponding first vectors and second vectors may be compared to determine the degree of collinearity. In some examples, linear regression may be used to fit a line to the plurality of centroids. The line may be considered a mean line or a trend of the plurality of centroids. In some examples, the degree of collinearity may be based on a standard deviation of the plurality of centroids from the line. For example, greater deviation of the centroids from the line implies less collinearity. In some examples, the degree of collinearity may be based on a root-mean-squared (RMS) error computation from a mean line the plurality of centroids.

The technique illustrated in FIG. 14 includes determining, by computing device 102, e.g., transformation module 130, whether each respective degree of collinearity is greater than a threshold (1306). In some examples, the threshold may include an amount of translation and/or rotation required for full collinearity. For example, the threshold may include a translation of less than about 1 millimeter and a rotation of less than about 10-degrees, such as less than about 5-degrees. In examples in which a line is fit to the centroids of an entire dental arch, the threshold may include a translation of less than about 20 millimeters, such as less than about 10 millimeters or less than about 1 millimeter. In examples in which a line is fit to a segment of a dental arch, the threshold may include a translation of less than about 10 millimeters, such as less than about 5 millimeters or less than about 1 millimeter. In examples in which a line is fit to a segment of a dental arch including only two teeth, the threshold may include a translation of substantially zero millimeters, e.g., zero or near zero within the limits of error of the scanners. In this way, collinearity may be used to reduce computational intensity or time by transforming only portions of data that require a threshold amount of transformation.

The technique illustrated in FIG. 14 includes dividing, by computing device 102, e.g., transformation module 130, each respective second group of the plurality of second groups into at least two subgroups (1308). Each respective second group may be defined as a parent group. The at least two subgroups may be defined as child groups.

The technique illustrated in FIG. 14 includes adjusting, by computing device 102, e.g., transformation module 130, an orientation of each respective second group of the plurality of second groups (1310). In some examples, adjusting the orientation may be based on a function of an original orientation of the respective second group and an orientation of a parent group. For example, adjusting the orientation may include translating and/or rotating each respective second group based on a weighted averaged of vectors representing a transformation of a parent group and a child group.

The technique illustrated in FIG. 14 includes iteratively determining centroids, determining degree of collinearity, adjusting orientation, and dividing each respective subgroups until each subgroup includes two crowns (1312).

Figure 15:
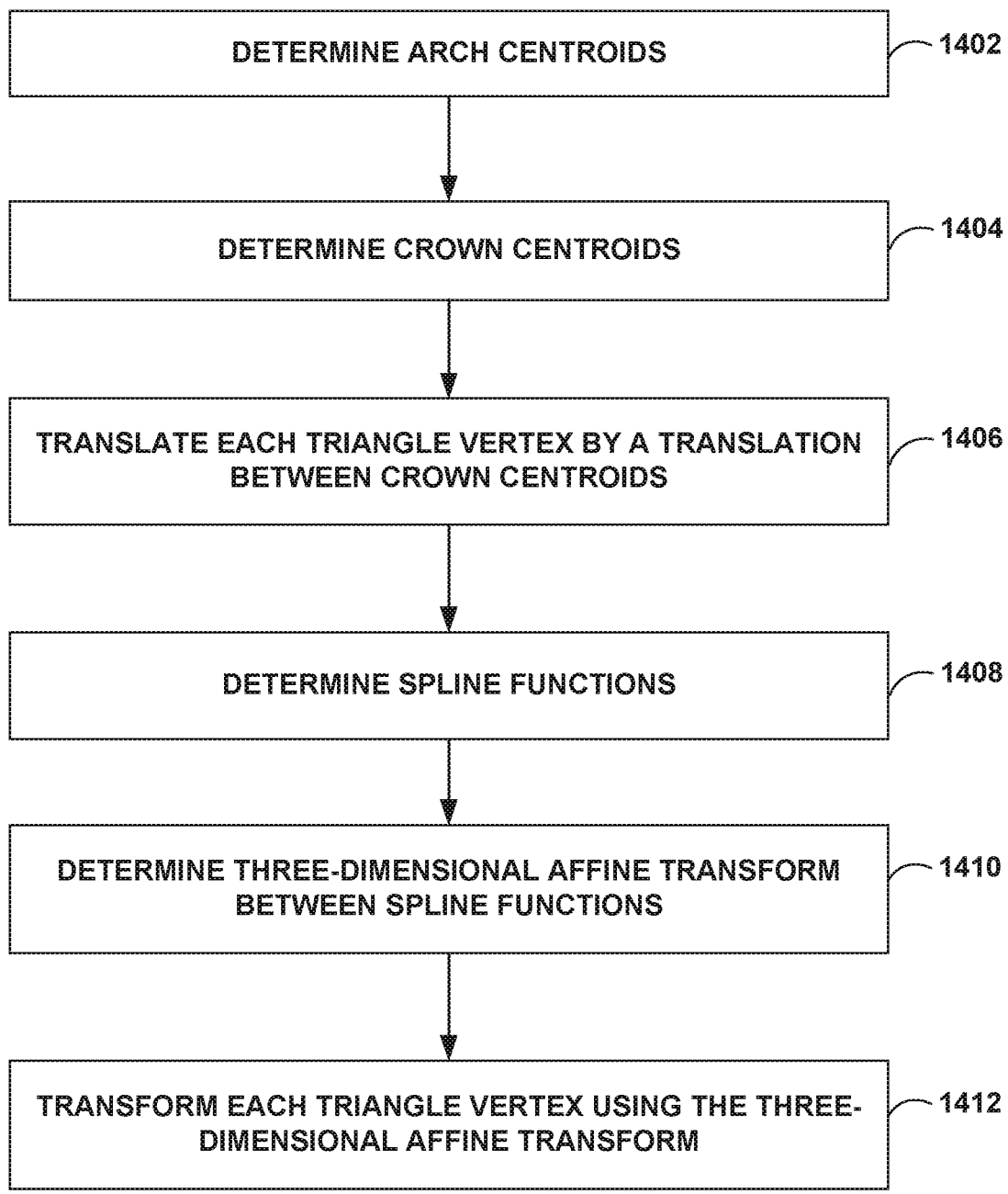
FIG. 15 is a flow diagram illustrating an example technique of transforming dental anatomy data.

FIG. 15 is a flow diagram of an example technique of transforming dental anatomy data. Although the technique of FIG. 15 will be described with respect to system 100 of FIG. 1, in other examples, the technique of FIG. 15 may be performed using a different system. Additionally, system 100 may perform other techniques for transforming dental anatomy data.

The technique illustrated in FIG. 15 includes determining, by computing device 102, e.g., transformation module 130, arch centroids of the volumetric dental data and superficial dental data (1402). The technique illustrated in FIG. 15 includes determining, by computing device 102, e.g., transformation module 130, crown centroids for each crown of the first spatial orientation of the crowns of the volumetric dental data and the second spatial orientation of the crowns of the superficial dental data (1404).

The technique illustrated in FIG. 15 includes translating, by computing device 102, e.g., transformation module 130, each triangle vertex of a mesh defining the second spatial orientation of the crowns of the superficial dental data by a translation between the crown centroids of the first spatial orientation of the crowns of the volumetric dental data and the corresponding crown centroids of the second spatial orientation of the crowns of the superficial dental data (1406).

The technique illustrated in FIG. 15 includes determining, by computing device 102, e.g., transformation module 130, a first spline function passing through the crown centroids of the first spatial orientation of the crowns of the volumetric dental data and a second spline function passing through the crown centroids of the translated second spatial orientation of the crowns of the superficial dental data (1408). The first and second spline functions may include any suitable piecewise polynomial parametric curve. For example, first and second spline functions may include three-dimensional spline functions or six-dimensional spline functions (e.g., which combine both translation and rotation components). In some examples, the first and second spline functions may include other interpolation functions.

The technique illustrated in FIG. 15 includes determining, by computing device 102, e.g., transformation module 130, a three-dimensional affine transform from the second spline function to the first spline function (1410). The three-dimensional affine transform may include any suitable number of parameters. For example, a 12-parameter affine transformation may be suitable to define a relationship between data representative of three-dimensional images, e.g., volumetric dental data and superficial dental data. The three-dimensional affine transform may include, but is not limited to, at least one of a translation component, a rotational component, or a scaling component.

In some examples, determining the three-dimensional affine transform may include determining, by computing device 102, e.g., transformation module 130, for each respective spline function of the first spline function at each of the crown centroids of the first spatial orientation of the crowns of the volumetric dental data and the second spline function at each of the crown centroids of the second spatial orientation of the crowns of the superficial dental data, a first vector tangent to the respective spline function, a second vector normal to the respective spline function and passing through the arch centroid, and a third vector equal to the cross product of the first vector and the second vector. The three-dimensional affine transform is based on the first vector, the second vector, and the third vector.

The technique illustrated in FIG. 15 includes transforming, by computing device 102, e.g., transformation module 130, each triangle vertex of a mesh defining the second spatial orientation of the crowns of the superficial dental data using the three-dimensional affine transform (1412). In some examples, transforming each triangle vertex using the three-dimensional affine transform may include a plurality of sub-steps. For example, the technique may include determining, by computing device 102, e.g., transformation module 130, a translation spline function that interpolates between translational components of the three-dimensional affine transform. The technique also may include determining, by computing device 102, e.g., transformation module 130, a rotation spline function that interpolates between rotational components of the three-dimensional affine transform. The technique also may include determining, by computing device 102, e.g., transformation module 130, a scaling spline function that interpolates between scaling components of the three-dimensional affine transform. Alternatively, the technique may include determining, by computing device 102, e.g. transformation module 130, a higher-dimensional spline function that simultaneously interpolates between at least one of translational components, rotational components, or scaling components of the three-dimensional affine transform. For example, a control point or key frame in the spline function may be represented by any subset of values in a transformation matrix comprising the three-dimensional affine transform, not just a 3-tuple for each of translation or rotation values, e.g. (x, y, z) or ($\alpha$, $\beta$, $\gamma$).

After determining the translation spline and rotation spline, the technique may include, for each triangle vertex of a mesh defining the second spatial orientation of the crowns of the superficial dental data projecting, by computing device 102, e.g., transformation module 130, the vertex onto a nearest point on the second spline function. The technique also may include defining, by computing device 102, e.g., transformation module 130, a plane normal to the second spline function that passes through the nearest point on the second spline function. The technique also may include determining, by computing device 102, e.g., transformation module 130, a value of the second spline function at an intersection of the plane and the nearest point on the second spline function. The technique also may include evaluating, by computing device 102, e.g., transformation module 130, the translation spline function and the rotation spline function at the value to determine at least one of a translation component, a rotation component, or a scaling component. The technique also may include defining, by computing device 102, e.g., transformation module 130, a vertex-specific three-dimensional affine transform comprising at least one of the translation component, the rotation component, or the scaling component. The technique also may include applying, by computing device 102, e.g., transformation module 130, the vertex-specific three-dimensional transform to the vertex.

In some examples, the combined dental data generated using the techniques illustrated in FIG. 5-14 may be used to manufacture dental appliances.

Figure 16:
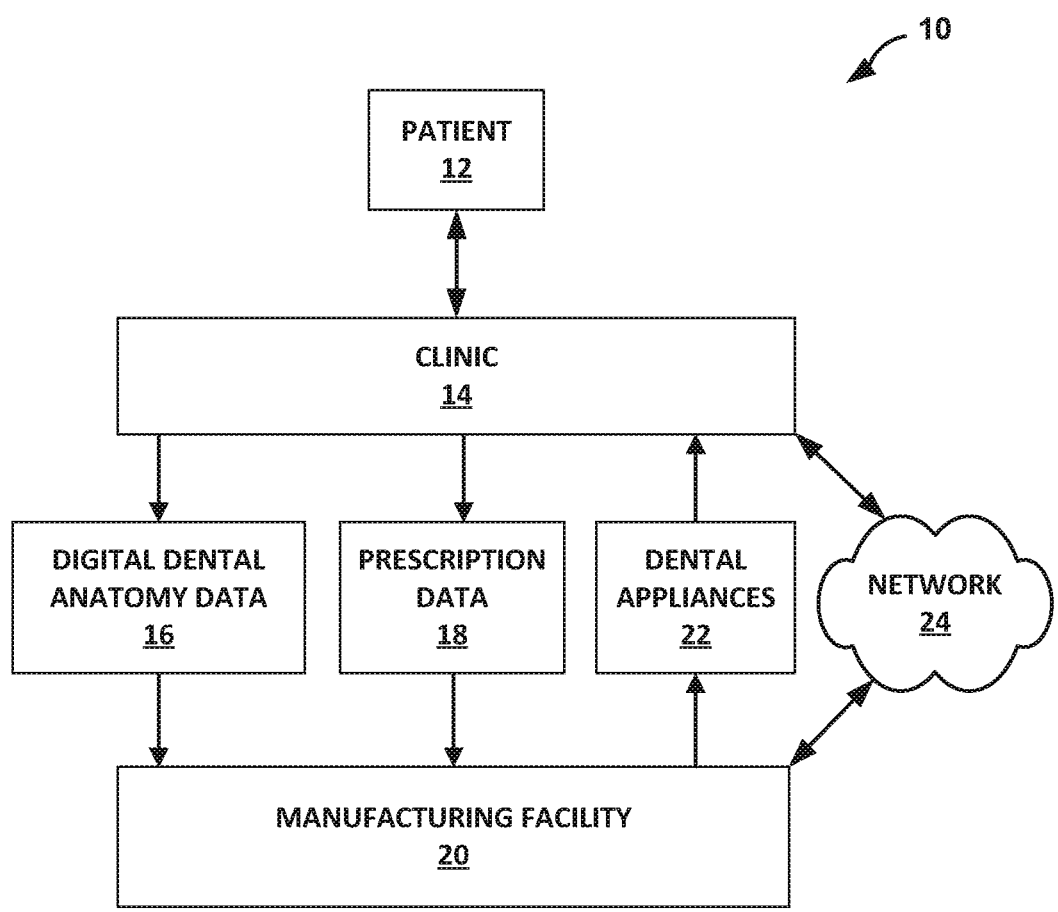
FIG. 16 is a block diagram illustrating an example computer environment.

FIG. 16 is a block diagram illustrating an example computer environment 10, in which clinic 14 and manufacturing facility 20 communicate information throughout a manufacturing process of dental appliance 22 for patient 12. The dental appliance 22 may include, for example, clear tray aligners, implants, prosthetics, or the like. Initially, an orthodontic practitioner of clinic 14 generates one or more images of the dental anatomy of patient 12 using, for example, first imaging device 106 and second imaging device 108 (FIG. 1), to generate volumetric dental anatomy data and superficial dental anatomy data. To generate digital dental anatomy data 16, a computer may transform raw data from the imaging systems into usable digital models using the techniques described above. Additionally, the computer may segment dentition surfaces to produce one or more discrete, movable 3D tooth object models representing individual teeth. The computer may further separate these tooth models from the gingiva into separate objects. Segmentation may allow a user to characterize and manipulate the teeth arrangement as a set of individual objects. In some examples, the computer may derive diagnostic information such as arch length, bite setting, interstitial spacing between adjacent teeth, and even American Board of Orthodontics (ABO) objective grading from these models. By replacing physical processes with digital processes, the data acquisition step and data manipulation steps can be executed at separate locations without the need to transport stone models or impressions from one location to another. Reducing or eliminating the need for shipping physical objects back and forth can result in significant cost savings to both customers and manufacturers of customized appliances.

After generating digital dental anatomy data 16, clinic 14 may store digital dental anatomy data 16 within a patient record in a database. Clinic 14 may, for example, update a local database having a plurality of patient records. Alternatively, clinic 14 may remotely update a central database (optionally within manufacturing facility 20) via network 24. After digital dental anatomy data 16 is stored, clinic 14 electronically communicates digital dental anatomy data 16 to manufacturing facility 20. Alternatively, manufacturing facility 20 may retrieve digital dental anatomy data 16 from the central database. Alternatively, manufacturing facility 20 may retrieve preexisting digital dental anatomy data 16 from a data source unassociated with clinic 14.

Clinic 14 may also forward prescription data 18 conveying general information regarding a practitioner's diagnosis and treatment plan for patient 12 to manufacturing facility 20. Manufacturing facility 20 may be located off-site or located with clinic 14. For example, each clinic 14 may act as manufacturing facility 20 such that a treatment plan and digital design may be performed entirely by a clinical practitioner, or an assistant, in the clinical setting, using software installed locally.

Manufacturing facility 20 utilizes digital dental anatomy data 16 of patient 12 to construct the dental appliances 22. The manufacturing may include 3D printing or other methods of additive manufacturing. A 3D printer allows manufacturing of intricate features of a dental appliance or a physical representation of the dental anatomy of patient 12. In some examples, other methods of additive manufacturing may include, for example, fused deposition modeling using a 5- or 6-axis cartesian robot or articulating arm robot to dispense material onto the surface of a removable dental appliance after thermoforming, 3D printing, and/or milling the removable dental appliance. Manufacturing may include post-processing, such as milling, to remove uncured resin and remove support structures, or to assemble various components, which may also be necessary and could also be performed in a clinical setting.

Sometime thereafter, manufacturing facility 20 forwards dental appliances 22 to clinic 14 or, alternatively, directly to patient 12. Patient 12 may return to clinic 14 for periodic monitoring of the progress of the treatment with removable dental appliances 22. During such periodic monitoring, a clinician may adjust the prescribed schedule of patient 12 for wearing the removable dental appliances in the set of removable dental appliances 22 sequentially over time. Monitoring generally includes visual inspection of the teeth of patient 12 and may also include imaging to generate new digital dental anatomy data 16.

Various examples have been described. These and other examples are within the scope of the following claims.

"Adjacent teeth" refers to teeth that are within 2 positions from the nearest pontic. For example, if the pontic is the upper right central incisor 11 using the FDI two-digit notation, then teeth 12, 13, 21, and 22 are considered adjacent teeth.

"Pontic" refers to an artificial tooth that replaces a missing natural tooth. Pontics can also be referred to as units when part of the removable restorative dental appliance.

"Removable dental appliance" refers to an appliance that is removable from the dentition of a patient and is used for orthodontic treatment. An example of a removable dental appliance includes clear tray aligners.

"Removable restorative dental appliance" refers to an appliance that is restorative for a patient's dentition and removable from the dentition without tools. The removable restorative dental appliance can be a dental replacement that incorporates a pontic (such as a dental bridge, or partial denture) or a retainer. Removable restorative dental appliances also can be anchored to abutment teeth or implants.

"Retainer" refers to an be a dental appliance used to hold teeth in their correct position especially following orthodontic treatment.

"Spline function" refers to a wide class of functions that are used in applications requiring data interpolation and/or smoothing.

LIST OF ILLUSTRATIVE EMBODIMENTS

1. A method comprising:
    receiving, by a computing device, volumetric dental data indicative of a three-dimensional sub-gingival dental anatomy of a patient;
    receiving, by the computing device, superficial dental data indicative of a three-dimensional superficial dental anatomy of the patient;
    segmenting, by the computing device, a first subset of the volumetric dental data representative of crowns of teeth of the patient from a second subset of the volumetric dental data representative of roots of the teeth, wherein the first subset of the volumetric dental data is indicative of a first spatial orientation of the crowns, and wherein the second subset of the volumetric dental data is indicative of a spatial orientation of the roots;
    segmenting, by the computing device, a first subset of the superficial dental data representative of the crowns from a second subset of the superficial dental data representative of the gingiva of the patient, wherein the first subset of the superficial dental data is indicative of a second spatial orientation of the crowns, and wherein the second subset of the superficial dental data is indicative of a spatial orientation of the gingiva;
    transforming, by the computing device, the first subset of the superficial dental data indicative of the second spatial orientation of the crowns such that the second spatial orientation of the crowns substantially aligns with the first spatial orientation of the crowns;
    generating, by the computing device, combined dental data by replacing the first subset of the sub-gingival data indicative of the first spatial orientation of the crowns with the transformed first subset of the superficial dental data indicative of the second spatial orientation of the crowns to stitch the transformed first subset of the superficial dental data indicative of the second spatial orientation of the crowns to the second subset of the volumetric dental data representative of the roots; and
    outputting, by the computing device and for display, image data based on the combined dental data.
2. The method of embodiment 1, wherein receiving the volumetric dental data comprises receiving, by the computing device, the volumetric dental data from a cone beam computed tomography scanner or a magnetic resonance imaging scanner.
3. The method of embodiment 1 or 2, wherein receiving superficial dental data comprises receiving, by the computing device, the superficial dental data from an intra-oral scanner.
4. The method of any one of embodiments 1 through 3, wherein the sub-gingival dental anatomy comprises at least one of a maxilla of the patient, a mandible of the patient, or a portion of a skull of the patient.

5. The method of any one of embodiments 1 through 4, wherein the superficial dental data comprises a triangular mesh representing the optically visible surfaces of at least a portion of a maxillary arch of the patient or a mandibular arch of the patient.

6. The method of any one of embodiments 1 through 5, wherein the volumetric dental data comprises a density-weighted point cloud that resolves hard tissues of the sub-gingival dental anatomy and soft tissues of the sub-gingival dental anatomy, wherein the hard tissues comprise at least one of enamel, dentin, cementum, alveolar bone, or cortical bone, and wherein the soft tissues comprise at least one of hard palate, gingiva, tongue, oral mucosa, periodontal ligaments, cartilage, muscle, or skin.

7. The method of any one of embodiments 1 through 6, wherein receiving the volumetric dental data further comprises filtering, by the computing device, the volumetric dental data using at least one density threshold based on at least one density of at least one of the hard tissues or the soft tissues.

8. The method of embodiment 7, wherein the at least one density threshold comprises an upper density limit and a lower density of at least one of enamel, dentin, cementum, alveolar bone, cortical bone, hard palate, gingiva, tongue, oral mucosa, periodontal ligaments, cartilage, muscle, or skin.

9. The method of any one of embodiments 1 through 8, wherein segmenting the first subset of the volumetric dental data from the second subset of the volumetric dental data comprises:
segmenting, by the computing device, the first spatial orientation of crowns from the spatial orientation of the roots by combining points of a point cloud indicative of at least one of enamel, dentin, cementum, or restorative materials; and
determining, by the computing device, a triangular vertex mesh that defines the outer surface of the combined points.

10. The method of any one of embodiments 1 through 9, the method further comprising:
defining, by the computing device, a first group comprising a portion of the first subset of the volumetric dental data and the second subset of the volumetric dental data; and
defining, by the computing device, a second group comprising a portion of the first subset of the superficial dental data, wherein the portion of the first subset of the superficial dental data corresponds to the portion of the first subset of the volumetric dental data.

11. The method of embodiment 10, wherein the first group comprises crowns of a maxillary arch or a mandibular arch of the volumetric dental data and corresponding roots of the maxillary arch or the mandibular arch of the volumetric dental data, and wherein the second group comprises crowns of the maxillary arch or the mandibular arch of the superficial dental data.

12. The method of embodiment 10 or 11, wherein the first group comprises a plurality of first groups, each first group comprising at least two crowns of the first subset of the volumetric dental data and at least two corresponding roots of the second subset of the volumetric dental data, and wherein the second group comprises a plurality of second groups, each second group comprising at least two crowns of the first subset of the superficial dental data.

13. The method of any one of embodiments 1 through 12, wherein transforming the second spatial orientation of the crowns of the superficial dental data comprises at least one of translating or rotating, by the computing device, the second spatial orientation of the crowns of the superficial dental data to substantially align the with the first spatial orientation of the crowns of the volumetric dental data.

14. The method of any one of embodiments 1 through 13, wherein transforming comprises applying a plurality of linear transforms to discrete segments of the corresponding portion of the second dental data or applying a nonlinear continuous transform to the corresponding portion of the second dental data.

15. The method of any one of embodiments 1 through 14, wherein transforming the second spatial orientation of the crowns of the superficial dental data comprises:
determining, by the computing device, based on the first spatial orientation of the crowns of the volumetric dental data, at least one of an arch centroid, one or more arch segment centroids, one or more tooth centroids, one or more crown centroids, one or more dental anatomical landmarks, one or more mesh vertices, one or more mesh triangles;
determining, by the computing device, based on the second spatial orientation of the crowns of the superficial dental data, at least one of an arch centroid, one or more arch segment centroids, one or more tooth centroids, one or more crown centroids, one or more dental anatomical landmarks, one or more mesh vertices, one or more mesh triangles; and
translating or rotating, by the computing device, the at least one of an arch centroid, one or more arch segment centroids, one or more tooth centroids, one or more crown centroids, one or more dental anatomical landmarks, one or more mesh vertices, one or more mesh triangles of the second spatial orientation of the crowns of the superficial dental data in a three-dimensional space to substantially align with the at least one of an arch centroid, one or more arch segment centroids, one or more tooth centroids, one or more crown centroids, one or more dental anatomical landmarks, one or more mesh vertices, one or more mesh triangles of the first spatial orientation of the crowns of the volumetric dental data.

16. The method of any one of embodiments 1 through 14, wherein transforming the second spatial orientation of the crowns of the superficial dental data further comprises:
determining, by the computing device, one or more crown centroids of the first spatial orientation of the crowns of the volumetric dental data and the second spatial orientation of the crowns of the superficial dental data;
determining, by the computing device, a translation between one or more crown centroids of the first spatial orientation of the crowns of the volumetric dental data and the corresponding one or more crown centroids of the second spatial orientation of the crowns of the superficial dental data;
translating, by the computing device, each triangle vertex of a mesh defining the second spatial orientation of the crowns of the superficial dental data by the translation;
determining, by the computing device, a horizontal rotation angle $\alpha$ between a first vector between a first crown and a second crown of the first spatial orientation of the crowns of the volumetric dental data and a second vector between a third crown and a fourth crown of the second spatial orientation of the crowns of the superficial dental data, wherein the first crown corresponds to the third crown and the second crown corresponds to the fourth crown;

rotating, by the computing device, each triangle vertex of the mesh defining the third crown by the horizontal rotation angle α using a centroid of the third crown as a rotation center;

determining, by the computing device, a vertical rotation angle θ between a third vector between the first crown and a centroid of the first spatial orientation of the crowns of the volumetric dental data and a fourth vector between the third crown and a centroid of the second spatial orientation of the crowns of the superficial dental data; and rotating, by the computing device, each triangle vertex of the mesh defining the third crown by the vertical rotation angle θ using the centroid of the third crown as a rotation center.

17. The method of embodiment 16, wherein transforming the second spatial orientation of the crowns of the superficial dental data further comprises repeating the horizontal rotation and vertical rotation for each crown of the second spatial orientation of the crowns of the superficial dental data.

18. The method of any one of embodiments 1 through 14, wherein transforming the second spatial orientation of the crowns of the superficial dental data further comprises:

determining, by the computing device, first centroids of each first group of the plurality of first groups and second centroids of each second group of the plurality of second groups;

determining, by the computing device, a translation between each first centroid and corresponding second centroid;

translating each triangle vertex of each mesh defining each second group of the plurality of second groups by the translation;

determining, by the computing device, a vertical rotation angle θ between a first vector between a respective first centroid and a centroid of the plurality of first groups and a second vector between a respective second centroid and a centroid of the plurality of second groups;

rotating, by the computing device, each triangle vertex of each mesh defining each second group of the plurality of second groups by the vertical rotation angle θ using the respective second centroid as a rotation center.

19. The method of embodiment 18, wherein transforming the second spatial orientation of the crowns of the superficial dental data further comprises repeating the vertical rotation for each second group of the plurality of second groups.

20. The method of any one of embodiments 1 through 14, wherein transforming the second spatial orientation of the crowns of the superficial dental data further comprises:

determining, by the computing device, first centroids of each first group of the plurality of first groups and second centroids of each second group of the plurality of second groups;

determining, by the computing device, a respective degree of collinearity of the first centroids and second centroids;

determining, by the computing device, whether each respective degree of collinearity is greater than a threshold; and adjusting, by the computing device, an orientation of each respective second group of the plurality of second groups as a function of an original orientation of the respective second group and an orientation of the respective second group and at least one other second group of the plurality of second groups;

dividing, by the computing device, each respective second group of the plurality of second groups into at least two subgroups;

iteratively determining centroids, determining degree of collinearity, adjusting orientation, and dividing each respective subgroups until each subgroup comprises two crowns.

21. The method of any one of embodiments 1 through 14, wherein transforming the second spatial orientation of the crowns of the superficial dental data further comprises:

determining, by the computing device, arch centroids of the volumetric dental data and superficial dental data;

determining, by the computing device, crown centroids for each crown of the first spatial orientation of the crowns of the volumetric dental data and the second spatial orientation of the crowns of the superficial dental data;

translating, by the computing device, each triangle vertex of a mesh defining the second spatial orientation of the crowns of the superficial dental data by a translation between the crown centroids of the first spatial orientation of the crowns of the volumetric dental data and the corresponding crown centroids of the second spatial orientation of the crowns of the superficial dental data;

determining, by the computing device, a first spline function passing through the crown centroids of the first spatial orientation of the crowns of the volumetric dental data and a second spline function passing through the crown centroids of the translated second spatial orientation of the crowns of the superficial dental data;

determining, by the computing device, a three-dimensional affine transform from the second spline function to the first spline function;

transforming, by the computing device, each triangle vertex of a mesh defining the second spatial orientation of the crowns of the superficial dental data using the three-dimensional affine transform.

22. The method of embodiment 21, wherein determining the three-dimensional affine transform comprises:

determining, by the computing device, for each respective spline function of the first spline function at each of the crown centroids of the first spatial orientation of the crowns of the volumetric dental data and the second spline function at each of the crown centroids of the second spatial orientation of the crowns of the superficial dental data, a first vector tangent to the respective spline function, a second vector normal to the respective spline function and passing through the arch centroid, and a third vector equal to the cross product of the first vector and the second vector; and determining, by the computing device, the three-dimensional affine transform based on the first vector, the second vector, and the third vector.

23. The method of embodiment 21 or 22, wherein transforming each triangle vertex of a mesh defining the second spatial orientation of the crowns of the superficial dental data using a three-dimensional affine transform comprises:
    determining, by the computing device, a translation spline function that interpolates between translational components of the three-dimensional affine transform;
    determining, by the computing device, a rotation spline function that interpolates between rotational components of the three-dimensional affine transform;
    for each triangle vertex of a mesh defining the second spatial orientation of the crowns of the superficial dental data:
        projecting, by the computing device, the vertex onto a nearest point on the second spline function;
        defining, by the computing device, a plane normal to the second spline function that passes through the nearest point on the second spline function;
        determining, by the computing device, a value of the second spline function at an intersection of the plane and the nearest point on the second spline function;
        evaluating, by the computing device, the translation spline function and the rotation spline function at the value to determine a translation component and a rotation component;
        defining, by the computing device, a vertex-specific three-dimensional affine transform comprising the translation component and the rotation component; and
        applying, by the computing device, the vertex-specific three-dimensional transform to the vertex.

24. A method comprising:
    receiving, by a computing device, first dental data indicative of a first three-dimensional dental anatomy of a patient;
    receiving, by the computing device, second dental data indicative of a second three-dimensional dental anatomy of the patient;
    segmenting, by the computing device, a first subset of the first dental data from a second subset of the first dental data, wherein at least a portion of the second dental data corresponds to the first subset of the first dental data;
    transforming, by the computing device, the corresponding portion of the second dental data to substantially align with the first dental data;
    generating, by the computing device, combined dental data by replacing the first subset of the first dental data with the transformed corresponding portion of the second dental data to stitch the transformed second dental data to the second subset of the second dental data; and
    outputting, by the computing device and for display, image data based on the combined dental data.

25. The method of embodiment 24, wherein the first three-dimensional dental anatomy includes a removable restorative dental appliance worn by the patient, wherein the removable restorative dental appliance is not being worn by the patient in the second three-dimensional dental anatomy.

26. The method of embodiment 24, wherein the second three-dimensional dental anatomy includes a removable restorative dental appliance worn by the patient, wherein the removable restorative dental appliance is not being worn by the patient in the first three-dimensional dental anatomy.

27. The method of embodiment 25, wherein the first subset of the first dental data includes volumetric dental data of the removable restorative dental appliance and the second subset of the first dental data includes volumetric dental data of a dentition of a patient.

28. The method of embodiment 25, performing at least one operation responsive to the generation of the combined dental data.

29. The method of any of the preceding embodiments, wherein transforming comprises applying a plurality of linear transforms to discrete segments of the corresponding portion of the first dental data.

30. The method of any of the preceding embodiments, wherein transforming comprises applying a nonlinear continuous transform to the corresponding portion of the first dental data.

31. The method of embodiment 30, wherein the nonlinear continuous transform comprises a spline function.

32. The method of any of the preceding embodiments, wherein the removable restorative dental appliance comprises a pontic.

33. The method of any of the preceding embodiments, wherein the removable restorative dental appliance comprises a retainer.

34. The method of embodiment 33, wherein the removable restorative dental appliance is a dental bridge (a fixed partial denture) comprising an anchoring portion.

35. The method of embodiment 33, wherein the three-dimensional (3D) dental anatomy of the patient further includes at least some portion of tooth roots, gingiva, periodontal ligaments (PDL), alveolar process, or cortical bone.

36. The method of any of the preceding embodiments, further comprising:
    accessing, by the computing device, a digital representation of the combined dental data;
    determining, by the computing device, dimensions and shapes of a removable dental appliance for the patient based on a treatment plan, the treatment plan excluding a segmented region comprising at least a portion of the removable restorative dental appliance from tooth position adjustments of adjacent teeth, wherein the wherein the removable dental appliance comprises:
        an appliance body configured to form at least partially surround a plurality of teeth of a dental arch of the patient, the appliance body comprising a unitary material defining a shell shaped to receive at least one tooth of the patient;
    wherein the dimensions and shapes of the removable dental appliance comprise: a position, dimension, and shape of the shell; and
    transmitting, by the computing device, a representation of the removable dental appliance to a computer-aided manufacturing system.

37. The method of embodiments 36, wherein the removable restorative dental appliance is a partial denture comprising a pontic surrounded by a denture substrate, the denture substrate is conformable to a gum or bone ridge of the patient;

wherein determining dimensions and shapes of the removable dental appliance incorporates dimensions of the denture substrate.

38. The method of embodiment 37, wherein excluding the sub no repositioning force is applied to the pontic but force is applied to the adjacent teeth.

39. The method of embodiment 37, wherein the treatment plan does not use the removable restorative dental appliance as an anchor to affect the positioning of the teeth.

40. The method of any of embodiments 36 to 39, wherein determining, by the computing device, dimensions and shapes of the removable dental appliance includes accepting input from a user, wherein the input influences at least one of the dimensions and shapes.

41. The method of any of embodiments 36 to 40, wherein determining, by the computing device, dimensions and shapes of the removable dental appliance includes automatically determining at least one of the dimensions and shapes.

42. The method of any of embodiments 36 to 41, wherein determining, by the computing device, dimensions and shapes of the removable dental appliance includes presenting a representation of the removable dental appliance to a user for review.

43. The method of any of embodiments 36 to 42, wherein transmitting the representation of the removable dental appliance includes sending a digital model of the removable dental appliance from the computing device to the computer-aided manufacturing system, and manufacturing at least a portion of the removable dental appliance with the computer-aided manufacturing system according to the digital model from the computing device.

44. The method of embodiment 43, wherein the computer-aided manufacturing system comprises a 3D printer, and at least a portion of the removable dental appliance is formed using the 3D printer.

45. The method any of embodiments 36 to 44, wherein the method further comprises determining, by the computing device, dimensions and shapes of each of an ordered set of a removable orthodontic appliances for the patient, the removable dental appliance being one of the ordered set of a removable orthodontic appliances for the patient, wherein each removable dental appliance in the ordered set of a removable orthodontic appliances is configured to incrementally reposition the teeth of the patient to a more advanced position than any one of the earlier removable dental appliances within the ordered set of a removable orthodontic appliances.

46. The method of claim 45, wherein the ordered set of a removable orthodontic appliances is configured to avoid repositioning any units from the segmented region.

47. The method of embodiment 36, wherein determining, by the computing device, dimensions and shapes of the removable dental appliance includes selecting, by the computing device, the dimensions and shapes of the removable dental appliance according to a set of predefined design constraints, the set of predefined design constraints including one or more of a group consisting of:

a minimum and a maximum localized force applied to the one or more teeth of the patient or the attachment when the removable dental appliance worn by the patient;

a minimum and a maximum rotational force applied to the one or more teeth of the patient or the attachment when the removable dental appliance worn by the patient;

a maximum force applied to any unit from the segmented region of the removable dental appliance;

a minimum and a maximum translational force applied to the one or more teeth of the patient or the attachment when the removable dental appliance worn by the patient;

a minimum and a maximum total force applied to the one or more teeth of the patient or the attachment when the removable dental appliance worn by the patient; and a minimum and a maximum stress or strain applied to the removable dental appliance when worn by the patient.

48. The method of any of embodiments 36 to 47, further comprising selecting, by the computing device, a material of the removable dental appliance.

49. The method of any of embodiments 45 to 48, wherein determining, by the computing device, dimensions and shapes of the removable dental appliance includes selecting a thickness of at least one portion of the appliance body to provide a stiffness suitable to reposition the one or more teeth of the patient from their initial positions to adjusted positions when the removable dental appliance is worn by the patient.

50. The method of any of embodiments 36 to 49, wherein determining, by the computing device, dimensions and shapes of the removable dental appliance includes modifying the initial positions of one or more teeth of the patient (excluding the segmented region and anchored off of the teeth of the patient) to produce a modified dental anatomy, wherein
the modified dental anatomy represents an incremental repositioning of the one or more teeth of the patient as compared to the initial positions of the one or more teeth of the patient, and the dimensions and shapes of the removable dental appliance conform to the modified dental anatomy.

51. The method of any of embodiments 36 to 50, wherein the shell comprises a surface defining a void internal to the shell and shaped to receive the at least one tooth in the desired position.

52. The method of any of embodiments 36 to 51, wherein the computing device includes a plurality of computing devices operably connected via one or more computer networks.

53. A computing device including a processor and a memory storing instructions that, when executed by the processor, configure the apparatus to perform the method of embodiment 24 to embodiment 52.

54. A computing device, the computing apparatus comprising:
a processor; and
a memory storing instructions that, when executed by the processor, configure the computing device to:
receive first dental data indicative of a first three-dimensional dental anatomy of a patient;
receive second dental data indicative of a second three-dimensional dental anatomy of the patient;
segment a first subset of the first dental data from a second subset of the first dental data, wherein at least a portion of the second dental data corresponds to the first subset of the first dental data;

transform the corresponding portion of the second dental data to substantially align with the first dental data;

generate combined dental data by replacing the first subset of the first dental data with the transformed corresponding portion of the second dental data to stitch the transformed second dental data to the second subset of the second dental data; and output for display image data based on the combined dental data.

55. The computing device of embodiment 54, wherein the instructions further configure the computing device to:

receive, by the computing device, a digital representation of the combined dental data;

determine, by the computing device, dimensions and shapes of a removable dental appliance for the patient based on a treatment plan, the treatment plan excluding a segmented region comprising at least a portion of the removable restorative dental appliance from tooth position adjustments of adjacent teeth, wherein the wherein the removable dental appliance comprises:

an appliance body configured to form at least partially surround a plurality of teeth of a dental arch of the patient, the appliance body comprising a unitary material define a shell shaped to receive at least one tooth of the patient;

wherein the dimensions and shapes of the removable dental appliance comprise:

a position, dimension, and shape of the shell; and transmit, by the computing device, a representation of the removable dental appliance to a computer-aided manufacturing system.

56. A non-transitory computer-readable storage medium that stores computer system-executable instructions that, when executed, configure a processor to perform the method of any of embodiments 1 to 53.

What is claimed is:

1. A method comprising:

receiving, by a computing device, volumetric dental data indicative of a three-dimensional sub-gingival dental anatomy of a patient;

receiving, by the computing device, superficial dental data indicative of a three-dimensional superficial dental anatomy of the patient;

segmenting, by the computing device, a first subset of the volumetric dental data representative of crowns of teeth of the patient from a second subset of the volumetric dental data representative of roots of the teeth, wherein the first subset of the volumetric dental data is indicative of a first spatial orientation of the crowns, and wherein the second subset of the volumetric dental data is indicative of a spatial orientation of the roots;

segmenting, by the computing device, a first subset of the superficial dental data representative of the crowns from a second subset of the superficial dental data representative of the gingiva of the patient, wherein the first subset of the superficial dental data is indicative of a second spatial orientation of the crowns, and wherein the second subset of the superficial dental data is indicative of a spatial orientation of the gingiva;

transforming, by the computing device, the first subset of the superficial dental data indicative of the second spatial orientation of the crowns such that the second spatial orientation of the crowns substantially aligns with the first spatial orientation of the crowns, wherein transforming the second orientation of the crowns of the superficial dental data includes:

determining, by the computing device, one or more first centroids based on the volumetric dental data and one or more second centroids based on the superficial data, where each of the one or more second centroids corresponds to a respective first centroid;

determining, by the computing device, a translation between each first centroid and the corresponding second centroid;

translating each triangle vertex of each mesh defining each crown in the superficial dental data by the determined translation;

determining, by the computing device, one or more rotation angles between each first centroid and the corresponding second centroid, wherein each of the one or more rotation angles specifies a rotation along a corresponding axis;

rotating, by the computing device, each triangle vertex of each mesh defining each crown in the superficial dental data by each of the one or more rotation angles using the respective second centroid as a rotation center;

generating, by the computing device, combined dental data by replacing the first subset of the sub-gingival data indicative of the first spatial orientation of the crowns with the transformed first subset of the superficial dental data indicative of the second spatial orientation of the crowns to stitch the transformed first subset of the superficial dental data indicative of the second spatial orientation of the crowns to the second subset of the volumetric dental data representative of the roots; and outputting, by the computing device and for display, image data based on the combined dental data.

2. The method of claim 1, wherein receiving the volumetric dental data comprises receiving, by the computing device, the volumetric dental data from a cone beam computed tomography scanner or a magnetic resonance imaging scanner.

3. The method of claim 1, wherein receiving superficial dental data comprises receiving, by the computing device, the superficial dental data from an intra-oral scanner.

4. The method of claim 1, wherein the sub-gingival dental anatomy comprises at least one of a maxilla of the patient, a mandible of the patient, or a portion of a skull of the patient.

5. The method of claim 1, wherein the superficial dental data comprises a triangular mesh representing the optically visible surfaces of at least a portion of a maxillary arch of the patient or a mandibular arch of the patient.

6. The method of claim 1, wherein the volumetric dental data comprises a density-weighted point cloud that resolves hard tissues of the sub-gingival dental anatomy and soft tissues of the sub-gingival dental anatomy, wherein the hard tissues comprise at least one of enamel, dentin, cementum, alveolar bone, or cortical bone, and wherein the soft tissues comprise at least one of hard palate, gingiva, tongue, oral mucosa, periodontal ligaments, cartilage, muscle, or skin.

7. The method of claim 1, wherein receiving the volumetric dental data further comprises filtering, by the computing device, the volumetric dental data using at least one density threshold based on at least one density of at least one of the hard tissues or the soft tissues.

8. The method of claim 7, wherein the at least one density threshold comprises an upper density limit and a lower density of at least one of enamel, dentin, cementum, alveolar bone, cortical bone, hard palate, gingiva, tongue, oral mucosa, periodontal ligaments, cartilage, muscle, or skin.

9. The method of claim 1, wherein segmenting the first subset of the volumetric dental data from the second subset of the volumetric dental data comprises:
   segmenting, by the computing device, the first spatial orientation of crowns from the spatial orientation of the roots by combining points of a point cloud indicative of at least one of enamel, dentin, cementum, or restorative materials; and
   determining, by the computing device, a triangular vertex mesh that defines the outer surface of the combined points.

10. The method of claim 1, the method further comprising:
   defining, by the computing device, a first group comprising a portion of the first subset of the volumetric dental data and the second subset of the volumetric dental data; and
   defining, by the computing device, a second group comprising a portion of the first subset of the superficial dental data, wherein the portion of the first subset of the superficial dental data corresponds to the portion of the first subset of the volumetric dental data.

11. The method of claim 10, wherein the first group comprises crowns of a maxillary arch or a mandibular arch of the volumetric dental data and corresponding roots of the maxillary arch or the mandibular arch of the volumetric dental data, and wherein the second group comprises crowns of the maxillary arch or the mandibular arch of the superficial dental data.

12. The method of claim 1, wherein transforming the second spatial orientation of the crowns of the superficial dental data comprises at least one of translating or rotating, by the computing device, the second spatial orientation of the crowns of the superficial dental data to substantially align the with the first spatial orientation of the crowns of the volumetric dental data.

13. The method of claim 1, wherein transforming comprises applying a plurality of linear transforms to discrete segments of the corresponding portion of the second dental data or applying a nonlinear continuous transform to the corresponding portion of the second dental data.

14. The method of claim 1, wherein transforming the second spatial orientation of the crowns of the superficial dental data comprises:
   determining, by the computing device, based on the first spatial orientation of the crowns of the volumetric dental data, at least one of an arch centroid, one or more arch segment centroids, one or more tooth centroids, one or more crown centroids, one or more dental anatomical landmarks, one or more mesh vertices, one or more mesh triangles;
   determining, by the computing device, based on the second spatial orientation of the crowns of the superficial dental data, at least one of an arch centroid, one or more arch segment centroids, one or more tooth centroids, one or more crown centroids, one or more dental anatomical landmarks, one or more mesh vertices, one or more mesh triangles; and
   translating or rotating, by the computing device, the at least one of an arch centroid, one or more arch segment centroids, one or more tooth centroids, one or more crown centroids, one or more dental anatomical landmarks, one or more mesh vertices, one or more mesh triangles of the second spatial orientation of the crowns of the superficial dental data in a three-dimensional space to substantially align with the at least one of an arch centroid, one or more arch segment centroids, one or more tooth centroids, one or more crown centroids, one or more dental anatomical landmarks, one or more mesh vertices, one or more mesh triangles of the first spatial orientation of the crowns of the volumetric dental data.

15. The method of claim 1, wherein:
   the one or more first centroids are one or more crown centroids of the first spatial orientation of the crowns of the volumetric dental data and the one or more second centroids are crown centroids of the second spatial orientation of the crowns of the superficial dental data;
   a first rotational angle in the one or more determined rotational angles is a horizontal rotation angle $\alpha$ between a first vector between a first crown and a second crown of the first spatial orientation of the crowns of the volumetric dental data and a second vector between a third crown and a fourth crown of the second spatial orientation of the crowns of the superficial dental data, wherein the first crown corresponds to the third crown and the second crown corresponds to the fourth crown;
   a second rotational angle in the one or more determined rotational angles is a vertical rotation angle $\theta$ between a third vector between the first crown and a centroid of the first spatial orientation of the crowns of the volumetric dental data and a fourth vector between the third crown and a centroid of the second spatial orientation of the crowns of the superficial dental data; and
   the rotating comprises rotating, by the computing device, each triangle vertex of the mesh defining the third crown by the horizontal rotation angle $\alpha$ using a centroid of the third crown as a rotation center and rotating, by the computing device, each triangle vertex of the mesh defining the third crown by the vertical rotation angle $\theta$ using the centroid of the third crown as a rotation center.

16. The method of claim 1, wherein
   a first rotational angle in the one or more determined rotational angles is a vertical rotation angle $\theta$ between a first vector between a respective first centroid and a second vector between a corresponding respective second centroid; and
   the rotating comprises rotating, by the computing device, each triangle vertex of each mesh defining each crown in the superficial dental data by the vertical rotation angle $\theta$ using the respective second centroid as a rotation center.

17. The method of claim 1, wherein transforming the second spatial orientation of the crowns of the superficial dental data further comprises:
   determining, by the computing device, a plurality of first groups, each first group including a subset of the first centroids;
   determining, by the computing device, a plurality of second groups, each second group including a subset of the second centroids;
   determining, by the computing device, a respective degree of collinearity of the first centroids and second centroids;
   determining, by the computing device, whether each respective degree of collinearity is greater than a threshold; and
   adjusting, by the computing device, an orientation of each respective second group of the plurality of second groups as a function of an original orientation of the respective second group and an orientation of the respective second group and at least one other second group of the plurality of second groups;

dividing, by the computing device, each respective second group of the plurality of second groups into at least two subgroups;

iteratively determining centroids, determining degree of collinearity, adjusting orientation, and dividing each respective subgroups until each subgroup comprises two crowns.

18. The method of claim 1, wherein transforming the second spatial orientation of the crowns of the superficial dental data further comprises:

determining, by the computing device, arch centroids of the volumetric dental data and superficial dental data;

determining, by the computing device, crown centroids for each crown of the first spatial orientation of the crowns of the volumetric dental data and the second spatial orientation of the crowns of the superficial dental data;

translating, by the computing device, each triangle vertex of a mesh defining the second spatial orientation of the crowns of the superficial dental data by a translation between the crown centroids of the first spatial orientation of the crowns of the volumetric dental data and the corresponding crown centroids of the second spatial orientation of the crowns of the superficial dental data;

determining, by the computing device, a first spline function passing through the crown centroids of the first spatial orientation of the crowns of the volumetric dental data and a second spline function passing through the crown centroids of the translated second spatial orientation of the crowns of the superficial dental data;

determining, by the computing device, a three-dimensional affine transform from the second spline function to the first spline function;

transforming, by the computing device, each triangle vertex of a mesh defining the second spatial orientation of the crowns of the superficial dental data using the three-dimensional affine transform.

19. The method of claim 18, wherein determining the three-dimensional affine transform comprises:

determining, by the computing device, for each respective spline function of the first spline function at each of the crown centroids of the first spatial orientation of the crowns of the volumetric dental data and the second spline function at each of the crown centroids of the second spatial orientation of the crowns of the superficial dental data, a first vector tangent to the respective spline function, a second vector normal to the respective spline function and passing through the arch centroid, and a third vector equal to the cross product of the first vector and the second vector; and determining, by the computing device, the three-dimensional affine transform based on the first vector, the second vector, and the third vector.

20. The method of claim 18, wherein transforming each triangle vertex of a mesh defining the second spatial orientation of the crowns of the superficial dental data using a three-dimensional affine transform comprises:

determining, by the computing device, a translation spline function that interpolates between translational components of the three-dimensional affine transform;

determining, by the computing device, a rotation spline function that interpolates between rotational components of the three-dimensional affine transform;

for each triangle vertex of a mesh defining the second spatial orientation of the crowns of the superficial dental data:

projecting, by the computing device, the vertex onto a nearest point on the second spline function;

defining, by the computing device, a plane normal to the second spline function that passes through the nearest point on the second spline function;

determining, by the computing device, a value of the second spline function at an intersection of the plane and the nearest point on the second spline function;

evaluating, by the computing device, the translation spline function and the rotation spline function at the value to determine a translation component and a rotation component;

defining, by the computing device, a vertex-specific three-dimensional affine transform comprising the translation component and the rotation component; and applying, by the computing device, the vertex-specific three-dimensional transform to the vertex.

* * * * *